(12) United States Patent
Abell

(10) Patent No.: US 12,163,703 B2
(45) Date of Patent: *Dec. 10, 2024

(54) SYSTEM AND METHOD OF CONTROLLING TEMPERATURE OF A MEDIUM BY REFRIGERANT VAPORIZATION AND WORKING GAS CONDENSATION

(71) Applicant: Thomas U. Abell, New Albany, IN (US)

(72) Inventor: Thomas U. Abell, New Albany, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/335,750

(22) Filed: Jun. 15, 2023

(65) Prior Publication Data

US 2023/0392834 A1 Dec. 7, 2023

Related U.S. Application Data

(60) Division of application No. 16/800,850, filed on Feb. 25, 2020, now Pat. No. 11,719,473, which is a
(Continued)

(51) Int. Cl.
*F25B 23/00* (2006.01)
*C12C 11/00* (2006.01)
(Continued)

(52) U.S. Cl.
CPC .............. *F25B 23/006* (2013.01); *C12G 1/00* (2013.01); *F25B 39/04* (2013.01); *F28D 1/0213* (2013.01);
(Continued)

(58) Field of Classification Search
CPC ................ F25B 9/002; F25B 2700/193; F25B 2700/2115; F25B 23/006
(Continued)

(56) References Cited

U.S. PATENT DOCUMENTS 2,240,284 A 4/1941 Buchanan
3,374,726 A 3/1968 Takayanagi
(Continued)

FOREIGN PATENT DOCUMENTS

CN 101784847 A 7/2010
CN 103228899 A 7/2013
(Continued)

*Primary Examiner* — Steve S Tanenbaum
(74) *Attorney, Agent, or Firm* — Seed IP Law Group LLP

(57) ABSTRACT

A system and method of controlling temperature of a medium by refrigerant vaporization, or working gas condensation, or a combination of both, the system including a container, at least one a working gas reservoir having at least one reservoir section that includes a wall with an exterior surface structured to be thermally coupled with a volume of the medium in the container and to provide a volume of medium thermal coverage in the container, a condensation apparatus to provide regulation of working gas condensation in the reservoir, whereby the working gas reservoir forms a vapor space in each of the at least one reservoir section in response to receiving the working gas and to the condensation apparatus regulation of condensation to enable working gas condensation at or near a selected temperature of the volume of medium in the container that is thermally coupled to the respective reservoir section.

19 Claims, 23 Drawing Sheets

HEATING VOLUMES WITH
MINIMAL COVERAGE
SPACING = 2 * R3

VOLUME OF HEATING COVERAGE

VOLUME OF HORIZONTAL LATTICE SECTION

Related U.S. Application Data continuation-in-part of application No. 16/502,611, filed on Jul. 3, 2019, now Pat. No. 11,709,006, which is a continuation-in-part of application No. 16/110,895, filed on Aug. 23, 2018, now abandoned.

(60) Provisional application No. 62/769,980, filed on Nov. 20, 2018, provisional application No. 62/746,751, filed on Oct. 17, 2018.

(51) Int. Cl.
| | | |
|---|---|---|
| *C12G 1/00* | (2019.01) | |
| *C12H 1/22* | (2006.01) | |
| *C12M 1/02* | (2006.01) | |
| *F25B 39/04* | (2006.01) | |
| *F28D 1/02* | (2006.01) | |

(52) U.S. Cl.
CPC .............. *C12C 11/006* (2013.01); *C12H 1/22* (2013.01); *C12M 41/18* (2013.01)

(58) Field of Classification Search
USPC .......................................................... 99/276
See application file for complete search history.

(56) References Cited

U.S. PATENT DOCUMENTS

| | | |
|---|---|---|
| 3,814,003 A | 6/1974 | Vacano |
| 4,164,902 A | 8/1979 | Maarleveld |
| 4,537,660 A | 8/1985 | McCord |
| 4,790,238 A | 12/1988 | Hsu |
| 6,125,736 A | 10/2000 | Marin |
| 6,279,457 B1 | 8/2001 | Francia |
| 6,805,885 B2 | 10/2004 | Francia |
| 7,111,471 B2 | 9/2006 | Yamasaki et al. |
| 7,685,715 B2 | 3/2010 | Rule |
| 7,870,891 B2 | 1/2011 | Rule |
| 8,881,795 B2 | 11/2014 | Rule |
| 2005/0016721 A1 | 1/2005 | Antonijevic et al. |
| 2005/0039605 A1 | 2/2005 | Michev |
| 2005/0077029 A1 | 4/2005 | Morales Cervantes et al. |
| 2005/0281911 A1 | 12/2005 | Del Monte et al. |
| 2008/0102160 A1 | 5/2008 | Snell et al. |
| 2008/0175951 A1 | 7/2008 | Rule |
| 2008/0289354 A1 | 11/2008 | Dudley et al. |
| 2010/0129490 A1 | 5/2010 | Williams et al. |
| 2011/0067437 A1 | 3/2011 | Song |
| 2011/0100040 A1 | 5/2011 | Bush et al. |
| 2013/0115333 A1 | 5/2013 | Crosato |
| 2014/0345317 A1 | 11/2014 | Sasaki et al. |

FOREIGN PATENT DOCUMENTS

| | | | |
|---|---|---|---|
| CN | 206817825 U | 12/2017 | |
| KR | 20-2015-0003652 U | 10/2015 | |
| TW | I251064 B | 3/2006 | |
| TW | I584339 B | 5/2017 | |
| WO | WO-0010922 A1 * | 3/2000 | ........... B01D 1/0047 |

* cited by examiner

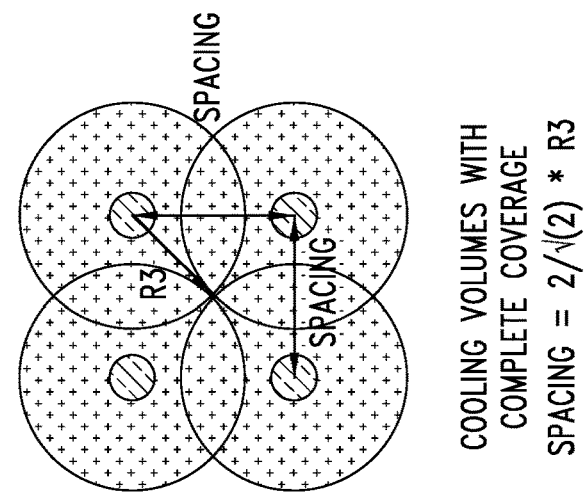
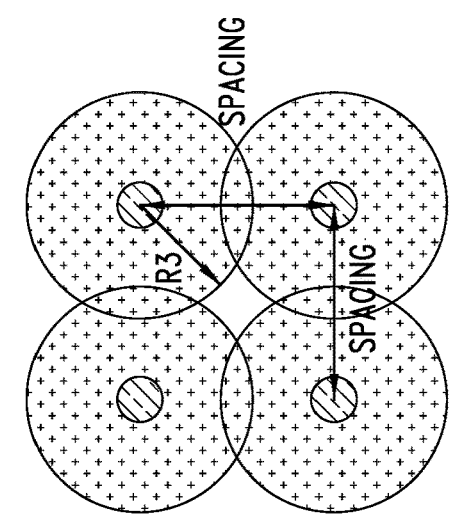
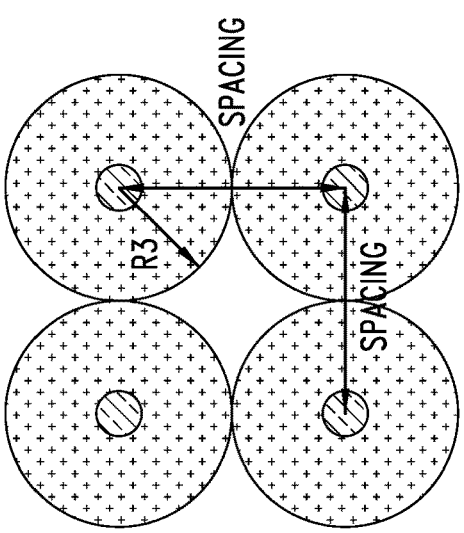

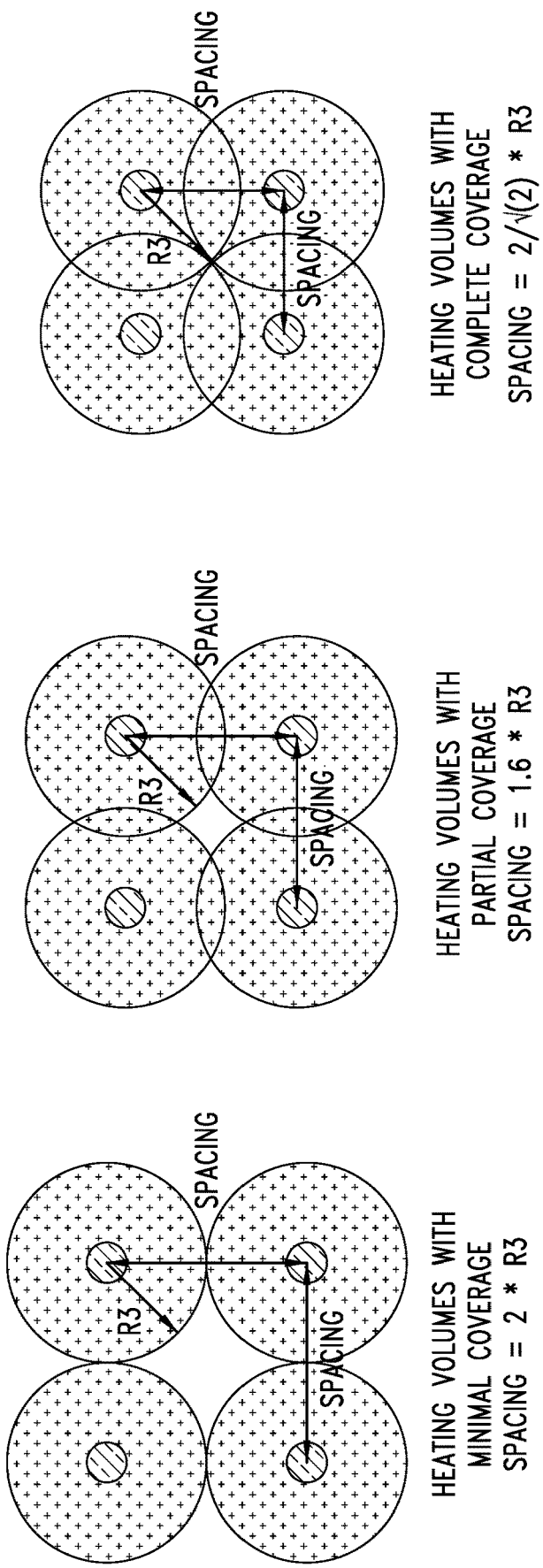

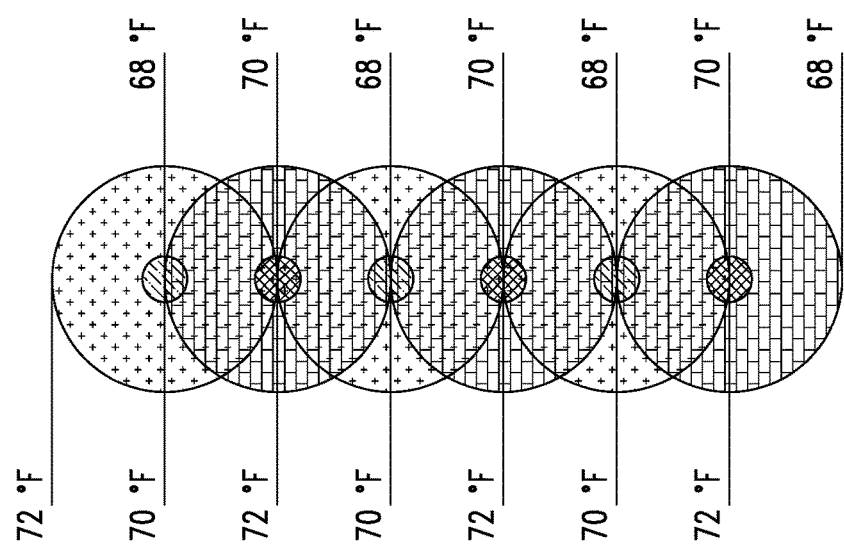
FIG. 31
FIG. 32
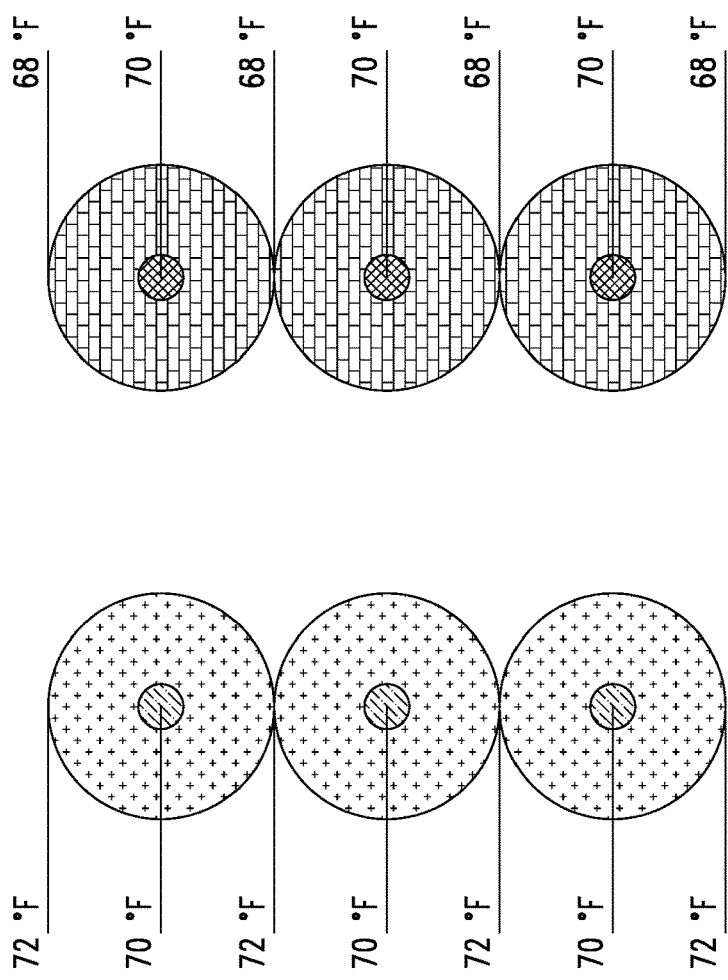
FIG. 30

SYSTEM AND METHOD OF CONTROLLING TEMPERATURE OF A MEDIUM BY REFRIGERANT VAPORIZATION AND WORKING GAS CONDENSATION

BACKGROUND

Technical Field

The present disclosure is directed to the process and tools used for dental restorations and, more particularly, to precise and efficient reconstruction and replacement of teeth using novel digital workflows and improved dental scan bodies, abutments and other dental devices that provide a more precise fit and optimal form and function.

Description of the Related Art

Temperature control is a fundamental requirement for successful chemical reaction engineering. Biological cells grow and produce products at an optimum temperature; likewise chemical catalysts, separations, crystallizations, evaporations, filtrations, polymerizations, isomerizations, and other reactions have specific operating temperatures which best achieve desired results.

Traditional cooling methods do not have the capability of adapting to the time and spatially dependent heat production characteristics of chemical and biochemical reactions, particularly those with low heat outputs. Such reactions include ethanol and lactic acid fermentations, anaerobic digestions, pharmaceutical cell cultures, biodiesel esterifications, and industrial polymerizations. Although these reactions can generate substantial instantaneous heat, the overall heat generated is low, and heat production values often vary significantly in time and space. This variation, also, may require local addition of heat to maintain a homogenous temperature profile throughout the reaction.

For example, fermentation of red wine has a heat output that increases rapidly in the first few hours, peaks briefly, and then falls gradually over several days. Fermentation heat output is also directly proportional to the local concentration of metabolically digesting yeast, concentrations which can vary spatially inside a tank or vessel. This variance is caused by dependence on naturally generated $CO_2$ for agitation/homogenization, with $CO_2$ production also directly proportional to the local concentration of metabolically digesting yeast and further proportional to the overall heat output of the fermentation cycle.

Failure to control the fermentation temperature of red wine may adversely affect batch quality. Specifically, yeast may clump on floating skins, generate localized areas of high heat/accelerated metabolic activity, and die prematurely due to elevated, local temperatures. These deaths then result in an insufficient yeast population to complete the conversion of all sugar in the tank or vessel (an incomplete/failed fermentation). Furthermore, failure to control temperature during fermentation can alter the flavor of the wine, due to changes in yeast metabolic selectivity for production of volatile metabolites.

Traditional temperature control methods for fermentation utilize an external cooling jacket with a variable flow of chilled water or glycol and a temperature control element submerged in the reaction vessel. While this method can provide rapid cooling of a vessel volume, quickly offsetting the heat of reaction, unnecessary cooling may follow. For example, a temperature element may correctly interpret a local need for cooling when the majority of the reaction volume does not require it. Likewise, an element may correctly determine that cooling of the nearby reaction volume is not required, when, in fact, the reaction has exceeded the set-point temperature elsewhere in the tank or vessel. Similar temperature control challenges are observed when heating of a reaction vessel is desired via an external heating jacket with a variable flow of hot water or steam and a temperature control element submerged in the reaction vessel.

One solution to this problem is agitation of the reaction volume. Agitation homogenizes the reaction volume and provides a more uniform concentration near the temperature element, better representative of the total vessel contents. However, many common biological reactions, like ethanol production during beer fermentation, are not artificially agitated as the yeast naturally generates $CO_2$, helping to homogenize the fermenting culture. Artificial agitation also risks accidental oxidation of the beer during fermentation, possibly altering the flavor profile and reducing shelf-life. The brewer thus must rely upon natural agitation but cannot be certain that the vessel cooling or heating system functions at optimal conditions due to lack of homogeneity in the fermenting volume.

As with wine fermentation, beer fermentation is also temperature sensitive. Generally, beer yeast can be divided into two categories: lagers and ales. Lager strains prefer temperatures between 45° F. and 55° F., while ale strains prefer fermentation temperatures between 60° F. and 70° F. Temperature control is crucial to ensure quality, particularly with regard to flavor and for consistency between fermenting batches. Temperature extremes, either above or below the desired range, risk both generation of unwanted chemical byproducts (esters, diacetyls, fusel alcohols, etc.) and thermal shock of the yeast, which can lead to cellular damage, including premature death.

Fermenters have been designed using conventional technology to utilize vacuum, water or air recirculation to cool tanks or vessels. For instance, U.S. Pat. No. 7,685,715 for methods for processing the contents of containers and tanks or vessels with a coaxial tank or vessels having an inner cylinder wrapped with spiral bands which are then covered by an outer cylinder whereby fluid is circulated between the cylinders to regulate the temperature of the inner cylinder and contents.

U.S. Patent Publication No. 20050077029 teaches heat exchanges for fermentation tanks or vessels using an outer cylinder with a concentric inner cylinder through which a liquid of a selected temperature is passed to regulate the temperature of the contents of the outer cylinder. U.S. Pat. No. 7,870,891 teaches using a jacketed fermenter using air as a cooling medium. U.S. Patent Publication No. 20080175951 teaches establishing a vacuum in the fermenter above the fermented liquid to control the vapor pressure.

BRIEF SUMMARY

The present disclosure is, in one implementation, directed to a system and method to control the temperature of a medium in a container, such as a tank or vessel.

In accordance with one implementation of the present disclosure, a system and method of controlling temperature of a medium by working gas condensation is provided. The system includes a container having an exterior and an interior, at least one working gas reservoir associated with the container, the at least one working gas reservoir having at least one reservoir section configured to hold working gas, each at least one reservoir section having a wall with an exterior surface structured to be thermally coupled with a volume of the medium in the container and to provide thermal change to the volume of the medium in the container and thereby provide a volume of medium thermal coverage in the container, the volume of medium thermal coverage having an outside boundary, a condensation apparatus to provide regulation of working gas pressure in the at least one working gas reservoir, and wherein the at least one working gas reservoir is configured to form a vapor space in each of the at least one reservoir sections in response to receiving working gas and in response to the condensation apparatus regulation of the working gas pressure to enable working gas condensation at or near a selected temperature of the volume of medium thermal coverage for the volume of the medium in the container that is thermally coupled to the respective at least one reservoir section.

In accordance with another aspect of the present disclosure, the at least one reservoir section includes a plurality of reservoir sections that each have a respective internal reservoir space that is in fluid communication with at least one other internal reservoir space of an adjacent reservoir section, and the plurality of reservoir sections are arranged in spaced relationship to adjacent reservoir sections with the respective volumes of medium thermal coverage having the respective boundaries of thermal coverage to be at least contiguous.

In accordance with a further aspect of the present disclosure, the system includes a working gas source in fluid communication with the working gas reservoir and the condensation apparatus and configured to provide working gas to the working gas reservoir in response to a change in pressure in the working gas reservoir as regulated by the condensation apparatus.

In accordance with still yet another aspect of the present disclosure, the plurality of reservoir sections are coupled together in series or in parallel or in a combination of series and parallel arrangements.

In accordance with an additional aspect of the present disclosure, the working gas reservoir comprises a lattice of reservoir sections.

In accordance with yet another additional aspect of the present disclosure, R3 is a radius of the volume of medium thermal coverage that is determined as follows:

$$R3 = \sqrt{\frac{1}{J*\pi}*(T2-T1)*\cfrac{1}{\cfrac{1}{2*\pi}*\left(\cfrac{1}{H1*R1}+\cfrac{\ln\left(\cfrac{R2}{R1}\right)}{K1}+\cfrac{1}{H2*R2}\right)}+R2^2}$$

where:
H1=Working gas heat transfer coefficient, including boundary layer effects (W/m²*K);
H2=Medium heat transfer coefficient, including boundary layer effects (W/m²*K);
J=Heat generated by medium per unit volume per unit time (W/m³);
K1=Thermal conductivity of working gas reservoir wall material of construction (W/m*K);
R1=Radius from center of reservoir section to interior of reservoir section wall (m);
R2=Radius from center of reservoir section to exterior of reservoir section wall (m);
R3=Radius from center of reservoir section to outside boundary of medium thermal coverage (m);
T1=Temperature of working gas at a location of condensation (K); and
T2=Temperature of the medium at an outer boundary of thermal coverage (K).

In accordance with another aspect of the present disclosure, a minimum spacing between a center of adjacent reservoir sections is not less than $$\frac{2}{\sqrt{2}}*R3$$

and in which R3 is a radius of the volume of medium thermal coverage. Ideally the at least one working gas reservoir is located in the interior of the container, although the at least one working gas reservoir is located on the exterior of the container.

In accordance with the present disclosure, a method of controlling a temperature of a medium by working gas condensation is provided. The method includes:
providing an apparatus for controlling the temperature of the medium by condensation of a working gas, the providing including providing:
a container having an exterior and an interior;
at least one working gas associated with the container, at one least working gas reservoir having at least one reservoir section configured to hold working gas, each at least one reservoir section having a wall with an exterior surface structured to be thermally coupled with a volume of the medium in the container and to provide thermal change to the volume of the medium in the container and thereby provide a volume of medium thermal coverage in the container, the volume of medium thermal coverage having an outside boundary;
a condensation apparatus to provide regulation of working gas pressure in the at least one working gas reservoir; and
wherein the at least one working gas reservoir is configured to form a vapor space in each of the at least one reservoir sections in response to receiving working gas and in response to the condensation apparatus regulation of working gas pressure to enable working gas condensation at or near a selected temperature of the volume of medium thermal coverage for the volume of the medium in the container that is thermally coupled to the respective at least one reservoir section;
introducing working gas into the at least one working gas reservoir to partially occupy the at least one reservoir section in the at least one reservoir section; and
regulating working gas pressure in the at least one reservoir section to enable working gas condensation at or near a selected temperature of the volume of medium thermal coverage for the volume of the medium in the container that is thermally coupled to the respective at least one reservoir section.

In accordance with another aspect of the foregoing method, the following steps are included:
partitioning the medium into localized thermal volumes; and
thermally coupling a working gas to respective localized thermal volumes to control a temperature of the localized thermal volume to maintain the medium at a selected temperature.

In accordance with a further aspect of the present disclosure, the partitioning the medium into localized thermal volumes includes positioning a working gas reservoir in physical proximity to the container, with at least one working gas reservoir section associated with a respective localized thermal volume.

In accordance with still yet another aspect of the present disclosure, the thermally coupling comprises regulating working gas pressure in each at least one reservoir section to maintain a temperature of the respective localized thermal volume at the selected temperature of the medium.

As will be readily appreciated from the foregoing, the present disclosure provides a system and method for controlling the temperature of a medium by providing localized temperature control of the medium. While representative implementations of the present disclosure are described in the context of fermentation, the system and method of the present disclosure will have application to both heating and cooling of a medium in order to maintain temperature in a wide variety of mediums, and is a novel approach to engineered temperature control that adjusts to both time and spatial variances in heat requirements without the need for advanced controls and programming. As opposed to traditional methods, which heat the entire system volume with maximum intensity but for varying lengths of time, the novel approach of the present disclosure adjusts temperature of only those spatial areas that, for example, require heating and with an intensity directly proportional to local heat loss. Cooling of the medium, then, is not accomplished directly, but rather through careful regulation of the net heat requirements of a reaction. The working gas pressure can be modulated to change the set-point temperature of medium and the present disclosure ensures that the allowable local changes in temperature never fall below that new set-point. Thus slow, deliberate cooling of the medium can be affected.

Traditional systems employ hot water or steam that activate whenever a measured set-point temperature has been exceeded. Activation is controlled by the local temperature near the sensing element and heating is accomplished rapidly through the use of large temperature gradients between the hot water or steam and system volume. Once a higher temperature set-point has been achieved, the heating system is then deactivated.

This approach has two distinct disadvantages: (1) The entire system volume is heated based upon a local subset of conditions, and (2) the entire system volume is subjected to large temperature gradients for the duration of the heating cycle. Thus, the system contents located at a distance from the sensing element are heated regardless of need, and system contents can be subject to thermal heat shock. This heat shock may be more pronounced for contents located near an external heating jacket or internal heating coil, particularly when the system volume lacks consistent agitation or homogenization.

The present disclosure avoids these disadvantages by using a working gas located in shallow, horizontal tubes, and connected by a common space. The working gas is held at or close to the desired temperature of the system volume and its condensation is controlled such that the working gas condenses at this same temperature. Because condensed liquid in the horizontal tubes is removed quickly and the tube vapor spaces remain connected, each horizontal section then condenses at approximately the same pressure/temperature as the horizontal sections above and below.

Temperature control of the system volume is affected by control of the condensation of the working gas. The working gas, when at its condensation point, will release a large amount of energy per unit volume as it changes phases to liquid but will also release this energy at constant temperature. Thus any local system volume near the horizontal tubes is protected from falling below the condensation temperature of the working gas therein, as long as those tubes contain working gas.

The present disclosure provides passive, continual, and continuous protection against a decrease in system volume, set-point temperature. A temperature sensing element is no longer required to activate the heating system, as local working gas condensation adds heat as soon as it is required and near the spatial point of requirement. Additionally, a high temperature gradient for heating is not required, as heat transfer must no longer be accomplished rapidly and across large distances (e.g., container wall to container center). As local heat requirement varies, the local temperature differential between the system volume and working gas coil also varies, and heat will be added proportionally by a waiting mass of local working gas.

In summary, the systems and methods of the present disclosure improve significantly on traditional temperature control methods. The approach no longer risks unnecessarily heating the entire system volume based upon conditions near a local, temperature sensing element or failing to activate that heating system, when needed, based upon local conditions near the sensing element. The present disclosure also avoids the need to create large temperature gradients that may risk thermal heat shock of system contents. Furthermore, controlled cooling of the medium can be affected using the reaction's own endothermic heat requirement without risk of overshoot and the possibility of thermal cold shock of system contents. Benefits of improved temperature control include optimized reaction rates, reduced undesirable side-reactions, and improved consistency between batches for batch processes.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein:

FIG. 4 is a cross-sectional illustration of multiple cooling volumes with minimal coverage in accordance with the present disclosure;

FIG. 5 is a cross-sectional illustration of multiple cooling volumes with partial coverage in accordance with the present disclosure;

FIG. 6 is a cross-sectional illustration of multiple cooling volumes with complete coverage in accordance with the present disclosure;

FIG. 20 is a cross-sectional illustration of multiple heating volumes with minimal coverage in accordance with the present disclosure;

FIG. 21 is a cross-sectional illustration of multiple heating volumes with partial coverage in accordance with the present disclosure;

FIG. 22 is a cross-sectional illustration of multiple heating volumes with complete coverage in accordance with the present disclosure;

FIG. 30 is a cross-sectional illustration of a radial temperature profile for adjacent refrigerant reservoirs;

FIG. 31 is a cross-sectional illustration of a temperature profile for adjacent working gas reservoirs; and FIG. 32 is a cross-sectional illustration of a temperature profile for the combination of adjacent refrigerant reservoirs and working gas reservoirs.

DETAILED DESCRIPTION

Figure 2:
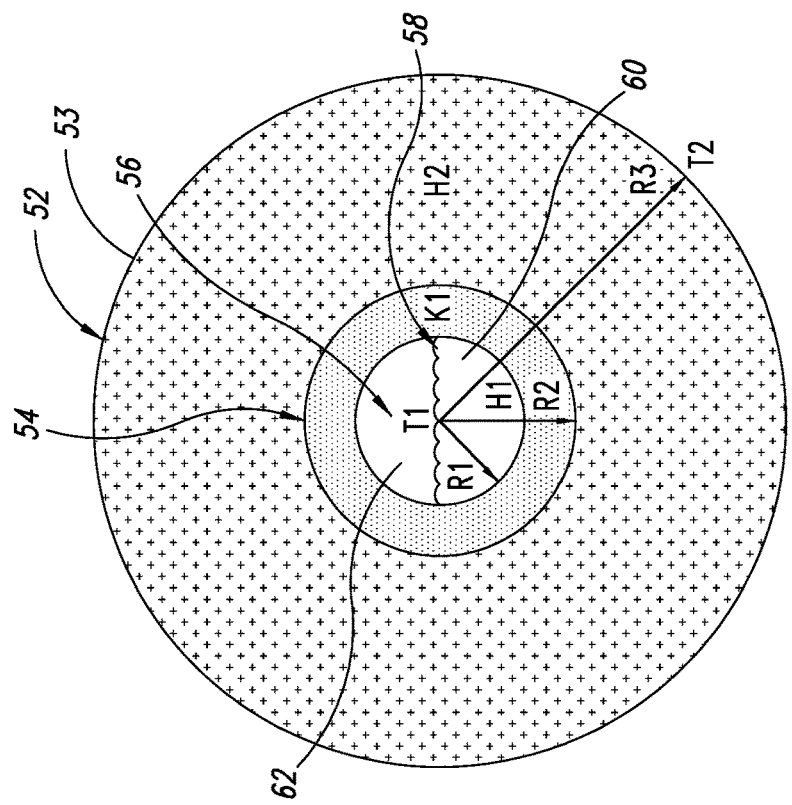
FIG. 2 is a cross-sectional illustration of radial heat transfer along the length of horizontal lattice section of FIG. 1.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with tanks or vessels, refrigerant, working gas, vaporization systems and vacuum systems, condensation systems, tubing, pipes, and coils have not been shown or described in detail to avoid unnecessarily obscuring descriptions of the implementations. Reference to "medium" is intended to include gas, liquid, solid, as well as gel and other states. Reference to "container" is intended to include, without limitation, tanks and vessels. In addition, reference to "pipe" or "tube" is intended to encompass conduits of various cross-sectional geometric configurations and conduits of any length unless otherwise specified herein.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one implementation" or "an implementation" means that a particular feature, structure or characteristic described in connection with the implementation is included in at least one implementation. Thus, the appearance of the phrases "in one implementation" or "in an implementation" in various places throughout this specification are not necessarily all referring to the same implementation. Furthermore, the particular features, structures, or characteristics may be combined in any suitable manner in one or more implementations. It will be appreciated that for simplicity and clarity of illustration, where considered appropriate, reference numerals may be repeated among the figures to indicate corresponding or analogous elements or steps.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the implementations.

In contrast to traditional temperature control methods, the present disclosure provides for both process heating and process cooling of a medium utilizing a minimum temperature gradient. While a gradient must be generated for successful transfer of heat in accordance with the present disclosure, this gradient does not need to be large due to the low heat transfer requirements of many common processes (for example, cell cultures) and if the heat can be removed as it is generated or applied continually. Moreover, large temperature gradients between a temperature control source and a target volume (i.e., medium) may actually damage the medium via thermal shock near the heating or cooling system interface. This can occur, for example, near the interior wall of jacketed, cell culture reactors.

Generally, the mechanical structure of some of the implementations of the present disclosure resembles a metal lattice work. In one aspect of the present disclosure, this structure is immersed in the volume requiring temperature control. Alternatively, this lattice work can be exterior to the container holding the medium. Ideally, lattice geometry, materials of construction and refrigeration system components are determined as a function of the medium to be cooled. However, with a given lattice geometry, material of construction, and working gas refrigeration system, cooling performance of structures formed in accordance with the present disclosure can be determined for any medium.

It is to be understood that while representative implementations of the present disclosure will be discussed in the context of cooling a medium, such as in the process of beer and wine fermentation, the systems and methods of the present disclosure will have application in other processes and in heating as well as cooling of various media.

The design of a lattice in accordance with the present disclosure has three primary aspects: (1) lattice internal dimensions, (2) lattice material of construction, and (3) spacing between adjacent lattice parts. All lattice designs have a common headspace and horizontally isolated sections holding volumes of liquid refrigerant. These characteristics ensure that refrigerant in each horizontal section evaporates at the same temperature and that there is always sufficient liquid refrigerant present to evaporate the heat generated nearby. Maintenance of liquid refrigerant height in each horizontal section is often a function of the orientation of that section with respect to gravity.

Theoretically, a lattice may be comprised of a series of horizontal sections of any shape and size, so long as those sections can store liquid refrigerant. Practically, it is most cost-effective to use a cylindrical pipe or tubing, by definition rated for the full vacuum conditions required of many refrigerants, instead of resorting to the advanced fabrication techniques required for odd-shaped, full-vacuum rated vessels. Also, it is ideal to maintain this pipe at a maximum of 70% full in order to provide sufficient surface area for liquid refrigerant vaporization from the interior surface of the headspace while still holding maximum liquid refrigerant volume inside the pipe/tubing. Additionally, free headspace allows unobstructed movement of the evaporated vapor along the length of the horizontal section to the vacuum source. The choice of lattice internal design is application specific, however, particularly with respect to refrigerant choice and refrigeration method (vacuum pump, compressor, etc.).

Theoretically, lattice material of construction is limited by the requirement that the material be mechanically compatible with the medium to be cooled and be compatible with operating conditions of the refrigerant trapped within. Practically, the material of construction is often determined by cleaning requirements (ex. sanitary requirements for cell cultures) and by those material thicknesses commercially available. The choice of lattice material of construction is application specific, however, and the thickness of material may be adjusted to improve heat transfer, despite the increased cost, for example.

Theoretically, spacing between adjacent lattice parts is a function of the medium to be cooled and its desired temperature profile and is also independent of horizontal length. For example, flavor profiles of a certain wine may be best produced at a range of 5° F., from 70° F. to 75° F., and spacing is then configured such that the outer lattice surface is held at 70° F. with a maximum of 75° F. to occur at the centerline between adjacent spacings. Practically, spacing between lattice sections is often a function of desired material of construction, welding costs, container geometry, ease of removal for maintenance, ease of cleanability, etc. An ideal spacing can be determined, however, by applying radial heat transfer equations to a horizontal coil section neglecting the length of that section (see drawings and derivations). Horizontal length, instead, is almost always determined by the need to provide the desired lattice spacing through the medium to be cooled and to ensure the presence of sufficient liquid volume of refrigerant in each horizontal section.

Use of a mathematical approach is preferred because ideal lattice spacing can be determined with a series of user-defined variables. A further advantage is that a complete lattice structure can be designed by examining the spacing requirements for a cross section of a single, horizontal lattice element.

If, for example, sanitary requirements require a specific material of construction, and the choice of refrigeration system require a certain refrigerant, both of these criteria can be incorporated into the spacing equation. Likewise, for an existing lattice structure and refrigeration system, the expected temperature gradient inside the medium to be cooled can be calculated for any medium type.

An important user-defined temperature variable is the maximum allowable temperature difference inside the medium to be cooled. For example, if a maximum temperature gradient of 5° F. and a maximum temperature of 75° F. is desired, ideal lattice spacing can be calculated using the derived equations described in more detail below, assuming a refrigerant vaporization temperature of 70° F. inside the lattice pipe and a centerline temperature of 75° F. in the medium between adjacent lattices.

The 5° F. value described is actually larger than the minimum temperature gradient required for successful heat transfer, however. In reality, this value is the total driving force required to drive heat from the furthest extent of medium to the location of refrigerant vaporization, a greater value than that required to drive heat only to the outer surface of the lattice.

This larger value actually has three components: (1) the temperature difference to transfer heat from the centerline between lattices, through the medium to be cooled, and to the surface of the lattice; (2) the temperature difference to transfer heat from the exterior surface of the lattice, through the lattice mechanical structure, and to its interior surface; and (3) the temperature difference to transfer heat from the interior surface of the lattice, through the liquid refrigerant, and to the liquid-vapor refrigerant interface where evaporation will occur.

More particularly, for heat transfer through a target medium, the maximum allowable temperature gradient is determined by the end-user. This value varies based upon the desired properties of the medium over the time-scale of cooling (ex. flavor profile). For a different medium and a fixed lattice spacing, the larger the gradient value, the greater that medium's resistance to heat flow. An increase in effective surface area for heat transfer from the medium to the lattice may reduce this gradient, however. Additional surface area may be created through the use of fin-type structures, attached to the outer surface of the lattice, for example.

The temperature gradient across the wall of the lattice mechanical structure is a function of the lattice material of construction and of its thickness. For a common lattice geometry and construction, this gradient value is constant, regardless of the medium to be cooled.

The temperature gradient from the interior wall of the lattice to the liquid-vapor refrigerant interface is a function of the chosen refrigerant and of the distance from the interior wall to the interface. For a known refrigerant and liquid refrigerant height inside the tube, this gradient value is constant, regardless of the medium to be cooled. Moreover, the headspace of a partially filled liquid refrigerant tube may form a thin liquid film of evaporating refrigerant on its interior surface, reducing the distance required for heat to travel from a percentage of the interior surface to the liquid-vapor interface. Purposeful roughing of the interior surface may also improve vaporization heat transfer, effectively reducing the temperature gradient required to drive an equivalent amount of heat from the interior wall to the liquid-vapor refrigerant interface.

For a given lattice geometry, materials of construction, and refrigeration system, a horizontal section is responsible for cooling an identical volume of medium. However, the heat generated by that volume may change as a function of the medium properties and thus the observed cooling performance of the lattice may change also.

Figure 1:
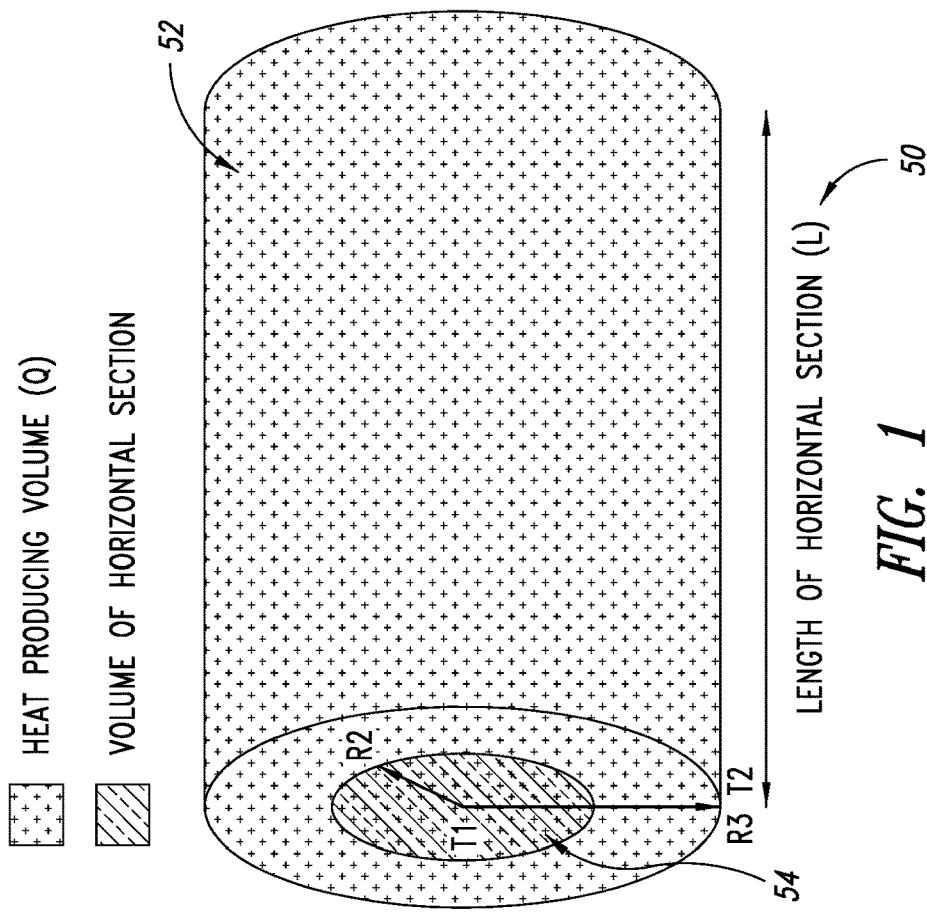
FIG. 1 is an illustration of radial heat transfer along a length of horizontal lattice section in accordance with the present disclosure.

Referring to FIGS. 1 and 2, for a given horizontal lattice section 50, the mechanical design must be capable of removing the maximum heat generated by a medium volume 52 surrounding that horizontal lattice section 50 that has an outside boundary 53. This volume can be approximated by assuming a cylindrical shape surrounding the horizontal lattice section 50 with a radius R3, the combination of the distance from lattice centerline to the tube exterior R2 and the distance from the lattice exterior to a centerline between adjacent lattices. The volume of the mechanical lattice is then subtracted from the total volume of the medium filled container to calculate the volume of the heat producing medium.

R1 is the inner radius of a lattice tube 54 and should be selected as a function of the refrigeration system desired. In a batch-fill system, each horizontal lattice tube 54 will need to retain enough refrigerant mass to absorb the maximum heat generated by the surrounding medium for a given time between fills (e.g., 1 hour). In a constant refill refrigeration system, this volume can be much smaller but is still subject to the criteria that sufficient refrigerant volume for vaporization remains throughout the entire horizontal length during maximum medium heat production.

With a value for R1 governed primarily by choice of refrigeration system, the horizontal length L of horizontal lattice sections 50 becomes the primary variable for establishing the refrigerant hold volume. In practice, the chosen length L per horizontal lattice section 50 almost always exceeds the minimum required, as this value is chosen primarily for structural support reasons, and to ensure that the minimum spacing requirement is satisfied throughout the medium.

Lattice geometry (spacing) varies based upon several variables, including medium, refrigerant, refrigeration method, and material of construction. Ideal spacing between adjacent lattice centerlines for production of wine, for example, would be roughly 6 inches using a lattice of 1" OD sanitary stainless tubing, ethanol refrigerant under vacuum, and with an allowable temperature variation of 5° F. A 10° F. allowable temperature variation would increase this ideal spacing to approximately 9 inches; a change from 1" to 2" OD tubing at the same 10° F. difference would further increase ideal spacing to roughly 12 inches.

Also, design consideration must be given to a pressure drop in a lattice headspace 56 during system operation. For example, in a batch fill system with a vacuum pump, the pressure at an interface 58 of liquid 60 and vapor refrigerant 62 will always be greater than the pressure at a vacuum source. Maintaining this pressure drop at a minimum is an important criterion of lattice design as it reduces the vacuum level that must be maintained at the vacuum source.

To illustrate, for 700 L of fermenting wine, a maximum liquid ethanol vaporization rate of 2 L/hr can be expected. This liquid mass vaporization corresponds to approximately 5 CFM of vapor generation at an 80° F. set-point temperature. With an allowable pressure drop due to system geometry of only 5%, 0.75" ID piping can be used to connect the headspace to the vacuum source, if the equivalent length of that piping (linear length and fittings) does not exceed approximately 115 ft.

Additionally, the lattice design and mathematical methodology can be adapted for use outside a container, in place of a cooling jacket. This might be beneficial, particularly for small diameter vessels, as the lattice would not be in contact with the end product and thus does not require cleaning between batches. However, this design may only be of practical use if the spacing between adjacent lattices is calculated near that of a container diameter.

An example of a mathematical derivation to determine ideal coil spacing is provided below:

$$V = I * R \text{ Electrical Analogy}$$

$$\Delta T = Q * R \text{ Heat Transfer Equation}$$

$$\frac{\Delta T}{L} = \frac{Q * R}{L} \text{ Divide by Length of Horizontal Section}$$

$$\frac{Q}{L} = \frac{\Delta T}{R * L} \text{ Rearrange}$$

L=Length of horizontal lattice section (m);
Q=Total heat transferred from medium to horizontal section per unit time (W);
R=Total resistance to heat transfer across the temperature differential per unit time (K/W); and
ΔT=Maximum temperature difference between medium and evaporating refrigerant (K).

$$\Delta T = T2 - T1 \text{ Temperature Differential } (K)$$

$$R = \left( \frac{1}{H1 * A1} + \frac{\ln\left(\frac{R2}{R1}\right)}{2 * \pi * L * K1} + \frac{1}{H2 * A2} \right) \begin{array}{l} \text{Resistance to} \\ \text{Heat Transfer} \\ (K/W) \end{array}$$

$$R = \frac{1}{2 * \pi * L} * \left( \frac{1}{H1 * R1} + \frac{\ln\left(\frac{R2}{R1}\right)}{K1} + \frac{1}{H2 * R2} \right) \text{ Substituting}$$

$$R * L = \frac{1}{2 * \pi} * \left( \frac{1}{H1 * R1} + \frac{\ln\left(\frac{R2}{R1}\right)}{K1} + \frac{1}{H2 * R2} \right) \begin{array}{l} \text{Resistance} \\ \text{to Heat} \\ \text{Transfer} \\ \text{Across} \\ \text{Length} \\ (K * m/W) \end{array}$$

$$Q = J * \left( \pi * R3^2 * L - \pi * R2^2 * L \right) \begin{array}{l} \text{Heat Generated by Medium} \\ \text{per Unit Time for a} \\ \text{Horizontal Section } (W) \end{array}$$

$$\frac{Q}{L} = J * \pi * (R3^2 - R2^2) \quad \begin{array}{l}\text{Heat Generated by Medium}\\ \text{per Length of Horizontal}\\ \text{Section per Unit Time } (W/m)\end{array}$$

A2=Surface area of exterior wall of horizontal lattice section (m$^2$);
H1=Refrigerant heat transfer coefficient, including boundary layer effects (W/m$^2$*K);
H2=Medium heat transfer coefficient, including boundary layer effects (W/m$^2$*K);
J=Maximum heat generated by medium per unit volume per unit time (W/m$^3$);
K1=Thermal conductivity of lattice material of construction (W/m*K);
R1=Radius from center of horizontal lattice section to inside of lattice wall (m);
R2=Radius from center of horizontal lattice section to outside of lattice wall (m);
R3=Radius from center of horizontal lattice section to outside of medium volume (m);
T1=Temperature at liquid-vapor refrigerant interface (K); and
T2=Temperature of medium at outer edge of medium volume (K).

$$\frac{Q}{L} * (R * L) - \Delta T = 0 \quad \begin{array}{l}\text{The Rearranged Heat Transfer}\\ \text{Equation Set Equal to Zero}\end{array}$$

$$J * \pi * (R3^2 - R2^2) * \frac{1}{2*\pi} *$$

$$\left(\frac{1}{H1*R1} + \frac{\ln\left(\frac{R2}{R1}\right)}{K1} + \frac{1}{H2*R2}\right) - (T2 - T1) = 0 \quad \text{Substituting}$$

$$R3 = \sqrt{\frac{\frac{1}{J*\pi}*(T2-T1)*}{\frac{1}{2*\pi}*\left(\frac{1}{H1*R1} + \frac{\ln\left(\frac{R2}{R1}\right)}{K1} + \frac{1}{H2*R2}\right)} + R2^2} \quad \begin{array}{l}\text{Setting}\\ \text{Equal}\\ \text{to } R3\end{array}$$

This equation can be solved for value R3, given user-defined values for all other variables. User-defined values can originate from published literature, previous design experience, allowable temperature variation in the medium, commercially available pipe/tubing sizes and thicknesses, etc. Note that this mathematical analysis is independent of the length of the horizontal section.

Figure 3:
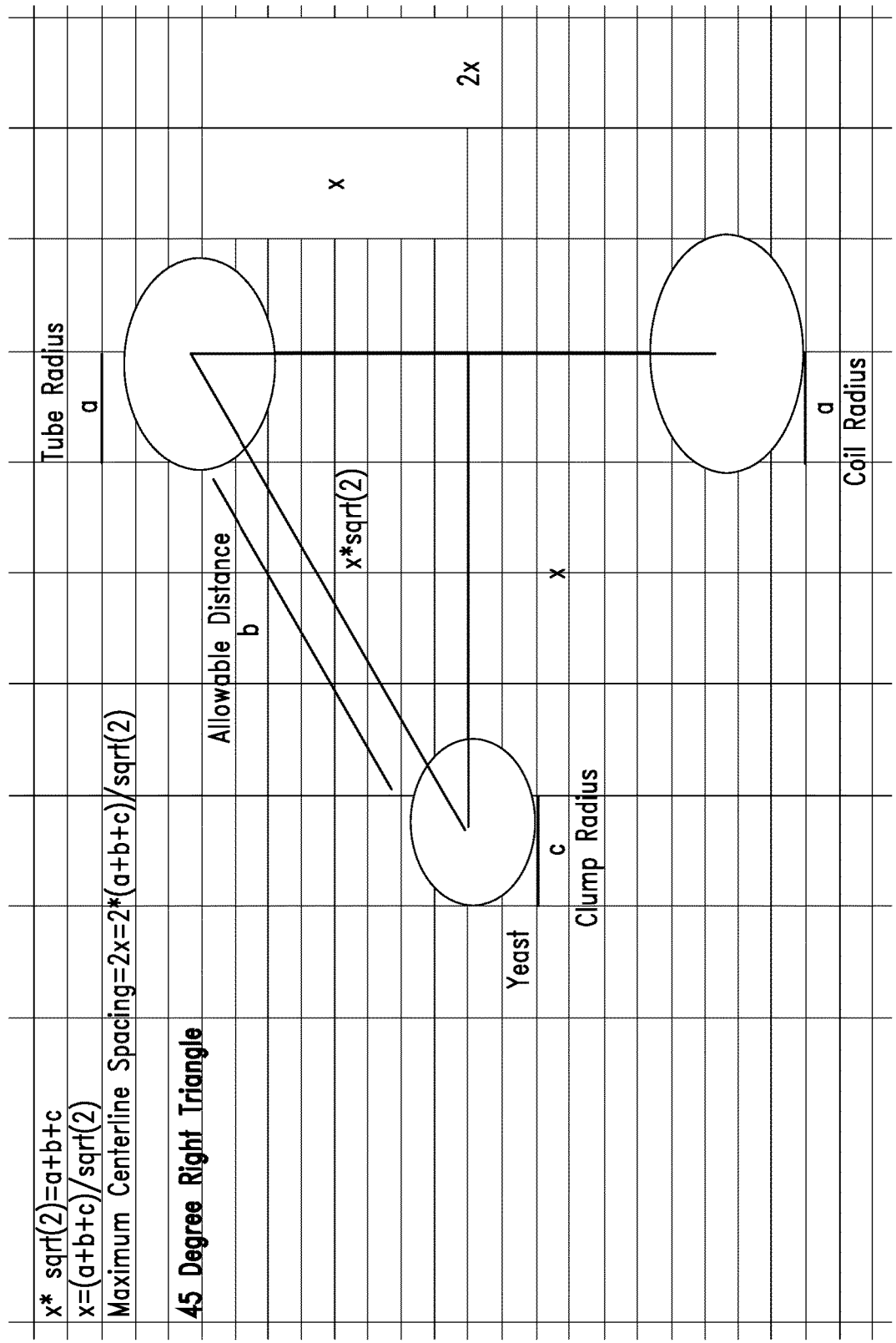
FIG. 3 is an illustration of the derivation of ideal spacing between lattice tubes calculated via right-angle geometry in accordance with the present disclosure.

With a known value for R3, the ideal spacing between tubes is calculated via right-angle geometry. The derivation of this equation is as shown in FIG. 3 Note that in this example, the variable R3 is equal to the sum of a+b+c, where "a" is the lattice pipe outer radius, "b" the distance between the lattice tube and a small clump of yeast cells, and "c" the radius of that clump. Total spacing between lattice tube centerlines is equal to $$\frac{2}{\sqrt{2}} * R3.$$

Also, this method assumes significant overlap of the radial cooling volumes between adjacent lattice sections such that no part of the medium volume can exceed the maximum temperature differential specified.

As shown in FIGS. 4-6, alternative geometric configurations can increase spacing between lattice sections, however, some part of the medium then may exceed the design temperature range due to insufficient cooling. FIG. 4 is a cross-sectional illustration of multiple cooling volumes with minimal coverage, FIG. 5 is a cross-sectional illustration of multiple cooling volumes with partial coverage, and FIG. 6 is a cross-sectional illustration of multiple cooling volumes with complete coverage.

Figure 7:
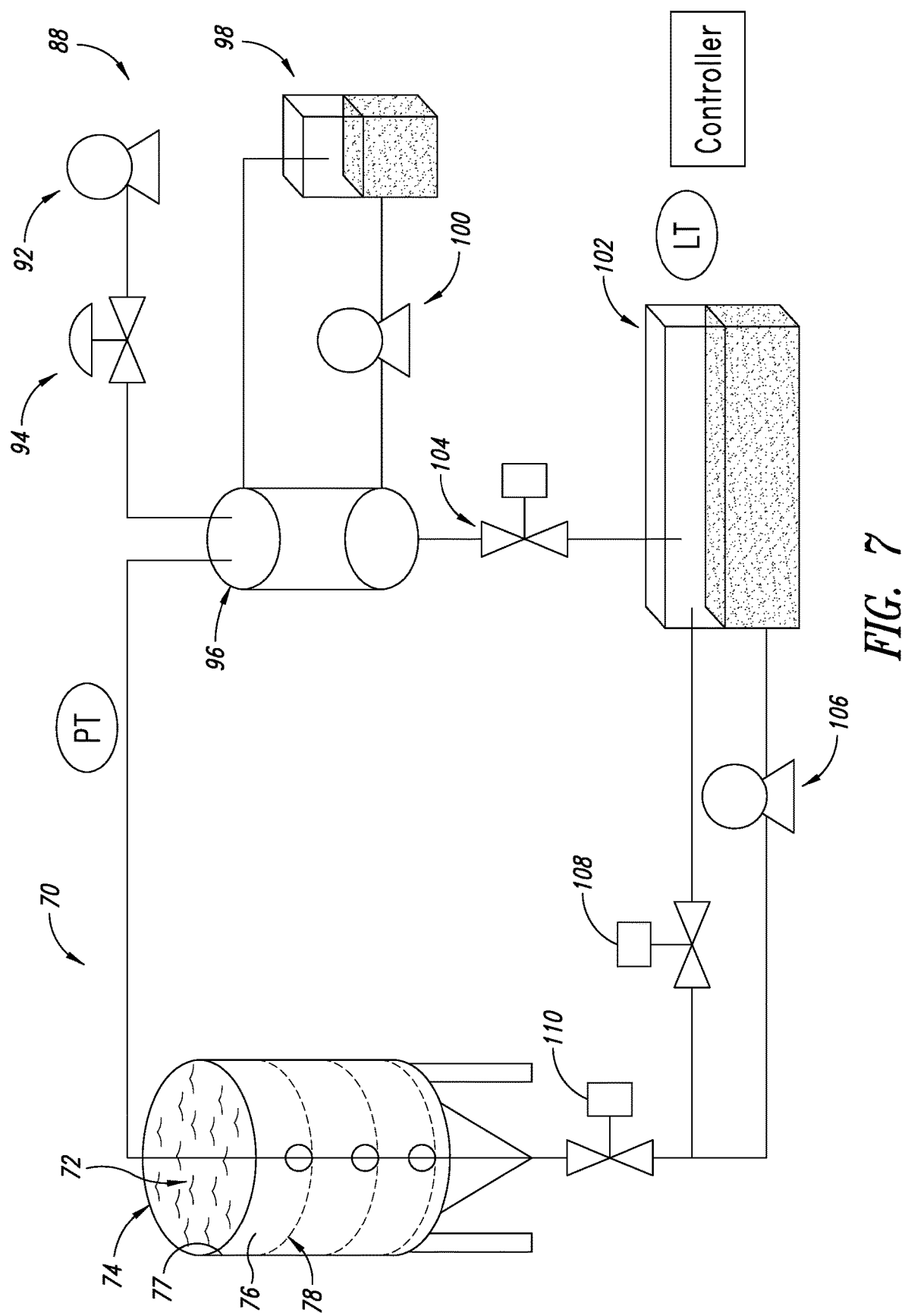
FIG. 7 is an illustration of a system formed in accordance with a representative implementation of the present disclosure.

FIG. 7 illustrates a system 70 to control the temperature of a medium 72 by refrigerant vaporization. In this representative implementation the system includes a container 74 having an exterior 76 and an interior 77. At least one a refrigerant reservoir 78 is associated with the container 74, the refrigerant reservoir 78 includes at least one reservoir section 80 structured to hold refrigerant 82 in an internal reservoir space 83. In this implementation there are a plurality of reservoir sections 80 as shown more clearly in FIGS. 8 and 9, each reservoir section 80 having a wall 84 with an exterior surface 86 structured to be thermally coupled with a volume of the medium in the container 74 and to provide thermal change to the volume of the medium in the container 74 and thereby provide a volume of medium thermal coverage 52 in the container as described above in connection with FIGS. 1-6 and to be described more fully below.

Each of the reservoir sections 80 has its respective internal reservoir space 83 in fluid communication with at least one other internal reservoir space 83 of an adjacent reservoir section 80, and the plurality of reservoir sections 80 are arranged in spaced relationship to adjacent reservoir sections 80 with the respective volumes of medium thermal coverage 52 having the respective boundaries of thermal coverage to be at least contiguous.

The system 70 further includes a vapor pressure apparatus 88 to provide regulation of refrigerant vapor pressure in the reservoir sections 80. The reservoir sections 80 are each configured to form a vapor space 90 in each reservoir section 80 in response to receiving refrigerant 82 and in response to the vapor pressure apparatus 88 regulation of vapor pressure above the refrigerant 82 to enable refrigerant vaporization at or near a selected temperature of the volume of medium thermal coverage 52 for the volume of the medium 72 in the container 74 that is thermally coupled to the respective reservoir section 80.

It is to be understood that the vapor pressure apparatus 88 can be implemented with readily available commercial equipment and hence will not be described in detail herein. Briefly, the vapor pressure apparatus 88 includes a vacuum pump 92 in fluid communication with the refrigerant reservoir 78. Ideally, a pressure regulator 94 is positioned between the vacuum pump 92 and the refrigerant reservoir 78. Control of the vacuum pump 92 can be performed manually or, more preferably, by automated controls that utilize sensors and a computer processor to process signals from the sensors and transmit control signals to the vacuum pump in response to the sensor signals.

In the implementation of FIG. 7, a condenser 96 is provided to condense a refrigerant, such as ethanol. The condenser 96 is in fluid communication with the refrigerant reservoir 78 to provide either a continuous or continual supply of refrigerant to the refrigerant reservoir 78. A chilled water tank 98 is coupled to the condenser 96 via a water pump 100 for fluid communication of water.

A refrigerant source, such as a refrigerant tank 102, is in fluid communication with the refrigerant reservoir 78 and the vapor pressure apparatus 88 and is configured to provide refrigerant 82 to the refrigerant reservoir 78 in response to a change in vapor pressure in the refrigerant reservoir 78 as regulated by the vapor pressure apparatus 88. The condenser 96 is also in fluid communication with the refrigerant tank 102 via a vent solenoid 104. In turn, the refrigerant tank 102 is coupled to the refrigerant reservoir 78 to supply refrigerant to the refrigerant reservoir 78 via a refrigerant pump 106 and in parallel with a drain solenoid 108. An isolation solenoid 110 is positioned between the refrigerant reservoir 78 and the parallel connection of the refrigerant pump 106 and the drain solenoid 108. The element LT is a level transmitter that senses and transmits an indication of the volume of refrigerant in the refrigerant tank 102. The element PT is a pressure transmitter that senses and communications an indication of the vapor pressure of the refrigerant in the vapor space.

In the implementation of FIG. 7, the refrigerant reservoir 78 is automatically refilled at regular intervals via the refrigerant pump 106 to replenish refrigerant 82 that has evaporated in order to provide temperature control of the medium 72. The vent solenoid 104 recovers refrigerant from the condenser 106 to the refrigerant tank 102. The vent solenoid 104 also provides a closed-loop path from the refrigerant pump 106 to the refrigerant tank 102 ensuring that the internal reservoir space 83 is completely filled with refrigerant 82. The drain solenoid 108 functions to remove excess refrigerant 82 from the refrigerant reservoir 78 to the refrigerant tank 102 via gravity, creating the vapor space 90.

Figure 8:
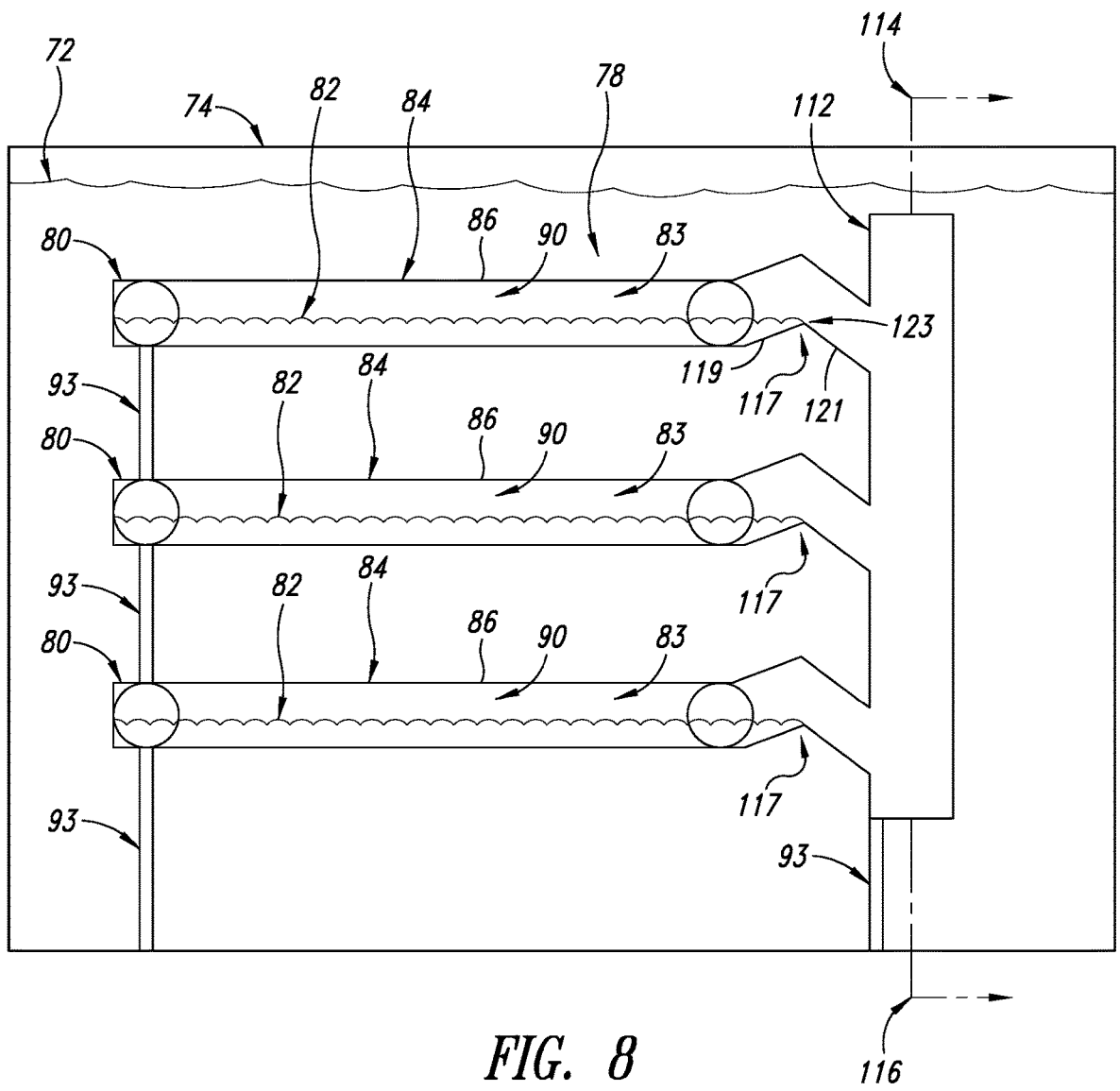
FIG. 8 is a cross-sectional side elevation of a refrigerant reservoir formed in accordance with the present disclosure and positioned in the interior of a container.
Figure 9:
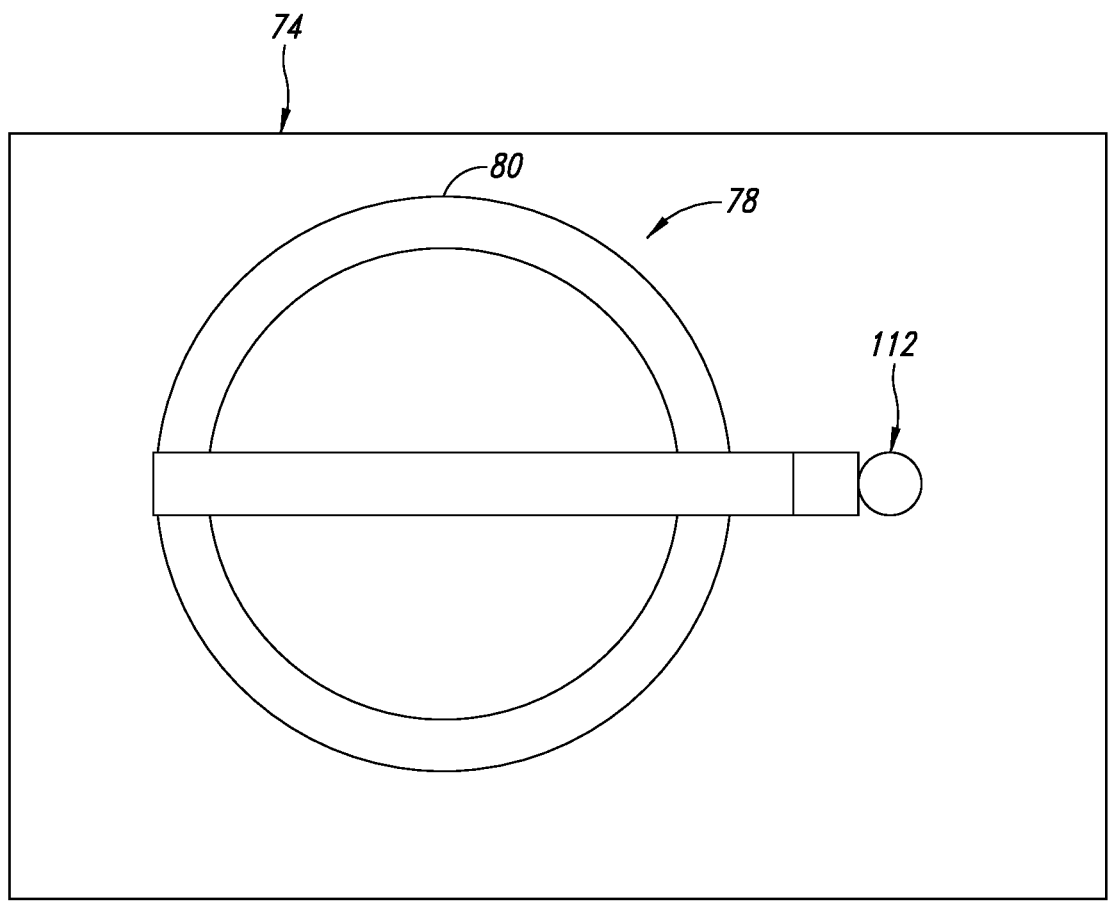
FIG. 9 is a top plan view of the refrigerant reservoir of FIG. 8.

As shown in FIG. 8, the refrigerant reservoir 78 in one implementation has a manifold 112 coupled to each of the reservoir sections 80 to provide fluid communication to an air vent line 114 and to a combination fill, drain, and vacuum line 116, which allows for system refrigerant fill and refrigerant drain, and system connection to the vacuum pump 92. The plurality of reservoir sections 80 may be coupled together in series or in parallel or in a combination of series and parallel arrangements. The refrigerant reservoir 78 in one implementation comprises a lattice of reservoir sections 80. Each reservoir section 80 is held in place by a vertical support 93 as is the manifold 112. Each reservoir section 80 includes at least one weir 117 in the respective reservoir section, with the weir 117 sized and shaped to divide the reservoir section into the vapor space 90 and a space for refrigerant 82. In this implementation, the weir 117 is a bent section of the tube or coil that forms the reservoir section 80, and the weir 117 includes a first wall 119 that angles upward to meet a second wall 121 that angles downward and form an apex 123. The apex 123 acts as a dam for the refrigerant 82, and its height in the reservoir section 80 determines how much refrigerant 82 will be retained in that reservoir section 80.

Figure 10:
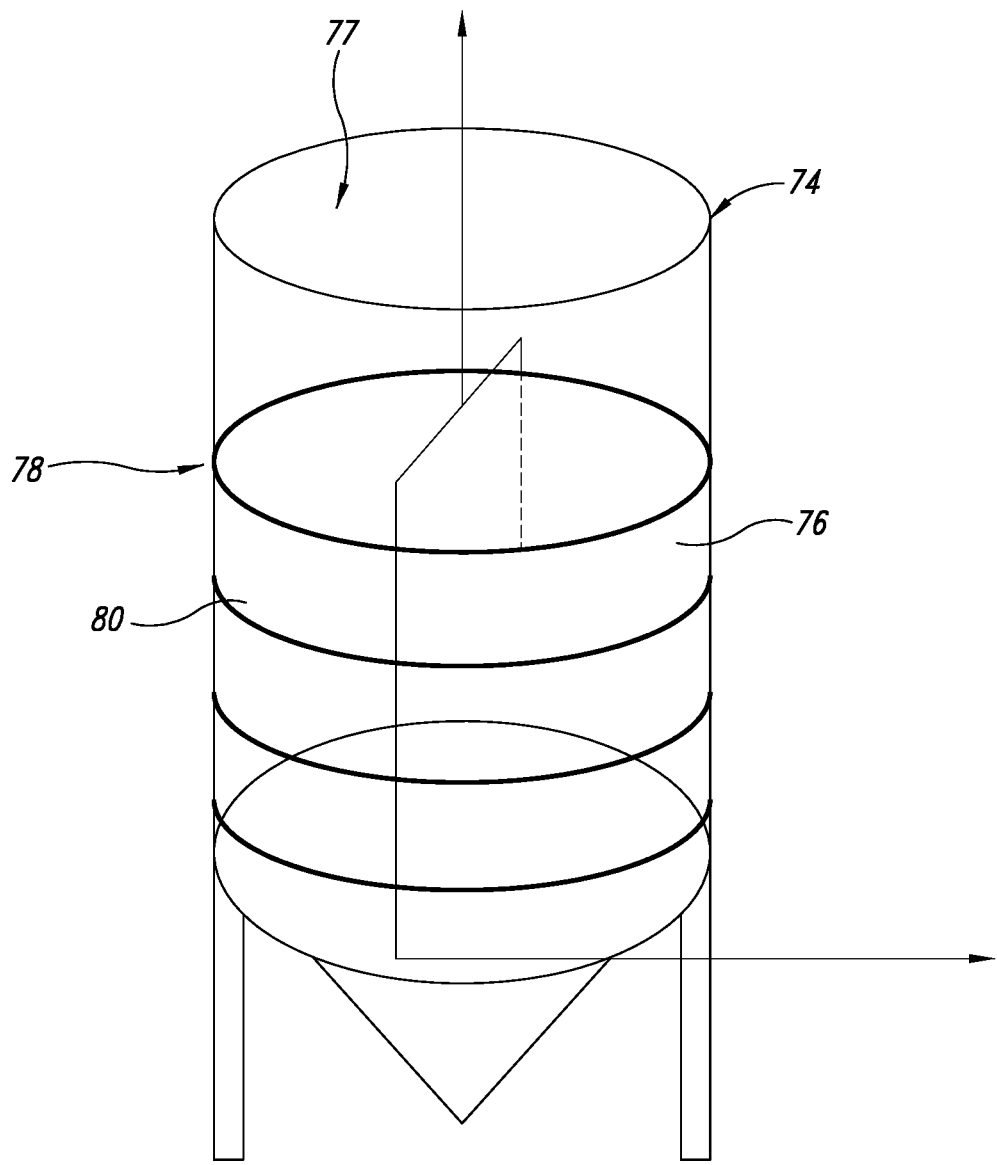
FIG. 10 is an illustration of a refrigerant reservoir on the exterior of a container in accordance with another implementation of the present disclosure.

In accordance with another aspect of the present disclosure, the refrigerant reservoir 78 may be located on the exterior of the container 74, which is shown in FIG. 10.

In operation, refrigerant 82 is introduced into the refrigerant reservoir 78 to partially occupy the reservoir sections 80 and form a vapor space 90 above the refrigerant 82 in the internal reservoir space 83 of each reservoir section 80. The vapor pressure above the refrigerant 82 in the refrigerant reservoir 78 is regulated to enable refrigerant vaporization at or near a selected temperature of the volume of medium thermal coverage 52 for the volume of the medium 72 in the container 74 that is thermally coupled to the respective reservoir section.

System operation requires that the refrigerant vaporize at a uniform or, preferably, an identical temperature throughout the coil. Also, a liquid refrigerant volume must be maintained throughout the coil, sufficient to remove via vaporization the heat generated by the medium. Proper orientation of the coil with respect to gravity ensures that the volume of liquid refrigerant therein matches the design intent of the coil weirs and dams. The coil metallurgy must be selected so as not to adversely affect the quality of the medium to be cooled, and the coil should be cleaned between uses to avoid possible contamination of the new medium to be cooled. Refrigerant vapor pressure should provide for refrigerant vaporization at or as close as possible to the desired temperature of the medium to be cooled, so as to avoid possible thermal shock of the medium.

In a batch type system with vacuum pump, the coil must be properly oriented with respect to gravity, filled with liquid refrigerant, drained to create a common headspace connecting the horizontal sections, and isolated to allow creation of a common vapor pressure space above all remaining liquid refrigerant inside. The vacuum pump is activated and a vacuum regulator allows adjustment of the refrigerant vapor pressure to match the desired heat removal profile for a given medium. The time between liquid refrigerant refills should be kept to a maximum, as during the refill sequence, the coil is unable to provide cooling. However, the time between refills must also be frequent enough to ensure that sufficient liquid refrigerant remains present in all sections of the coil so as to provide the desired volume of medium thermal coverage. Selection of refrigerant vapor pressure and time between refills is a function of the heat production profile of the medium to be cooled with respect to time. Ideally, during refill, the temperature of fresh liquid refrigerant should be at or near the desired set-point temperature of the medium to be cooled so as to avoid thermal shock of the medium.

In a continuous style system with traditional refrigerant compressor, proper orientation of the coil with respect to gravity ensures optimal system performance, as the refrigerant liquid volumes are then maintained at design in each horizontal section. The common vapor headspace is then likewise maintained at design. Compressor performance must also be monitored relative to the heat production profile of the medium with respect to time. Most importantly, the compressor must be capable of continued operation at variable flowrates of vapor refrigerant and throughout the desired range of refrigerant vapor pressures. Cell cultures, for example, can vary in heat production rate as a function of both time and batch number. System monitoring must be sufficiently robust to adjust system operation to unexpected swings in process variables without risk of damage to the compressor and associated components.

Refrigerant selection is a function of the heat production profile and optimal production temperature of the medium to be cooled relative to the choice of cooling equipment. For example, in a batch style system with vacuum pump and ethanol refrigerant, it is difficult to maintain operating pressures below 0.15 psia (pounds per square inch absolute) due to the pressure drop between the vacuum source and the coil during system operation. However, 0.15 psia corresponds to an ethanol refrigerant vaporization temperature of approximately 40° F., thus the vacuum pump and ethanol refrigerant combination is best suited for those applications which maintain the medium to be cooled at or above 40° F. After installation, pressure drop between the vacuum source and the coil must again be calculated as a function of system geometry to ensure that the selected refrigerant will vaporize at the desired temperature to allow for successful system operation. Operationally, the refrigerant vapor pressure corresponds to the refrigerant vaporization temperature. The objective is to control the vapor pressure of the refrigerant in the coil at a specific vaporization temperature, at or near that of the set-point temperature of the medium to be cooled.

For fermentation of wine, common maximum allowable temperature ranges are 64-77° F. for red wines and 50-59° F. for whites. Assuming an ethanol refrigerant and vacuum pump combination, these temperature ranges correspond to vapor pressures of approximately 0.232-0.288 psia for red wines and 0.184-0.213 psia for white wines. Assuming an R-134a refrigerant and compressor combination, these temperature ranges correspond to vapor pressures of approximately 77.10-96.11 psia for red wines and 59.98-70.61 psia for white wines.

For fermentation of beer, common maximum allowable temperature ranges are 60-70° F. for ales and 45-55° F. for lagers. Assuming an ethanol refrigerant and vacuum pump combination, these temperature ranges correspond to vapor pressures of approximately 0.217-0.256 psia for ales and 0.169-0.200 psia for lagers. Assuming an R-134a refrigerant and compressor combination, these temperature ranges correspond to vapor pressures of approximately 71.87-85.48 psia for ales and 54.62-65.72 psia for lagers.

The system must also provide cooling for the duration of the fermentation cycle. For primary fermentation of both red and white wines, 3-5 days is commonly required. For primary fermentation of beer, 1-2 weeks is commonly required for ales and 1-2 months is commonly required for lagers.

It will be appreciated that the present disclosure can be implemented in various systems, apparatus, and devices for a number of applications. These include, without limitation:

1. Artificial generation of convective currents to promote thermosiphon agitation/homogenization of the medium via vaporizing refrigerant held at different pressures.
2. Use of vaporizing refrigerant to indicate the spatial location of heat transfer.
3. Use of a buffer cooling fluid to improve the consistency of heat transfer, where the buffer fluid is in thermal contact with both the refrigerant reservoir and the medium.
4. Generation of currents inside the vaporizing refrigerant to improve heat transfer by variation of vapor pressure.
5. Pre-heat of the refrigerant, before supply to the vaporization apparatus, to provide heating of the medium such that both heating and vaporization cooling can be affected by the same refrigerant vaporization apparatus.
6. Use of a heat transfer medium, without condensation or vaporization, to approximate the functionality of a condensing working gas or a vaporizing refrigerant, via monitoring of the change in heat transfer fluid temperature between the supply from and return to the spaced apparatus.
7. Use of a condensing working gas to create localized thermal volumes for heating of a medium, where coil spacing is governed by the same principles and equations as for a vaporizing refrigerant.
8. Use of an intermediate medium, such as a plastic, metal, gel, or coating, exterior to the surface of the working gas reservoir or refrigerant reservoir, where the intermediate medium is in contact with both the surface of the working gas reservoir or refrigerant reservoir and the medium.
9. The combination of working gas reservoirs and refrigerant reservoirs to provide simultaneous heating and cooling of the medium.
10. Utilization of working gas condensation apparatuses and refrigerant vaporization apparatuses inside agitated tanks.

Each of these implementations is described in more detail below and in connection with the accompanying figures.

Figure 11:
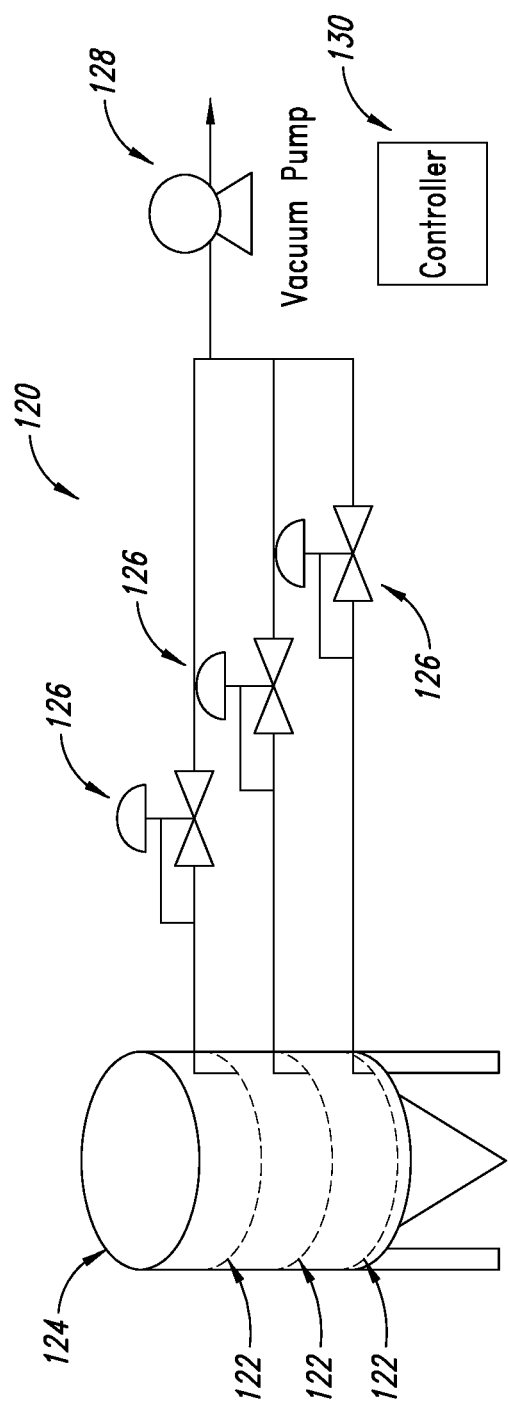
FIG. 11 is an illustration of a system formed in accordance with a representative implementation of the present disclosure in which pressure control by zones is affected by multiple pressure regulators.

1. Artificial Generation of Convective Currents to Promote Thermosiphon Agitation/Homogenization of the Medium Via a Condensing Working Gas or a Vaporizing Refrigerant Held at Different Pressures As shown in FIG. 11, a system 120 is shown having multiple vertically arranged coil sections 122 within a container 124. The control of the different vertical coil sections 122 at different vacuum pressures is accomplished by using regulators 126 and pressure sensors (not shown), which may be manual or automatic, and which are coupled to a vacuum pump 128. They can be used to alter current flows inside the medium in the container 124, such as beer, improving heat transfer from the beer to the coil surface. They can also be used to control agitation of the beer through a thermo-siphon effect.

An electronic controller 130 that is coupled to the sensors, pressure regulators 126, and vacuum pump 128. The construction of the electronic controller 130 is within the ability of those of ordinary skill in this technology and will not be described in detail herein. Briefly, an on-site hard wired controller or a remote wireless controller, such as an app on a portable computing or portable communication device, such as a cell phone, tablet, and the like is provided to communicate with the components to monitor conditions and provide control signals thereto. Controlled agitation is important in fermentation, transfer, and storage and the pressures may be either fixed or cycled and automated control and maintenance of head space pressure for the cooling medium can be regulated. A single, pressure control set-point is possible for all reservoir head space via a pressure transmitter measuring head space pressure and electronic communication with the vacuum source. The reservoir head space may also be divided into sections, such that separate portions of the cooling medium reservoir can be controlled in different zones at differing pressures.

In accordance with one aspect, thermo-siphon agitation can be utilized for homogenization during fermentation and to maintain this homogenization during the lager aging phase (during and after the cold crash to near 32° F.). Thermo-siphon agitation may be optimized to control strong wort movement during fermentation, increasing the contact efficiency between yeast and wort.

The reservoir of the heat exchanger is in fluid communication with a cooling medium supply and vacuum source such that the cooling medium fills the reservoir leaving a selected amount of head space. The reservoir is also in fluid communication with the vacuum source for pulling a vacuum of a desired level in the reservoir head space, providing for a controlled vacuum vaporization at a low temperature at or near that of the medium (such as beer). Assuming an ethanol refrigerant, the vacuum level would be between 0.169 psi and 0.200 psi for lagers, equivalent to a fermentation temperature of 45° F.-55° F., and between 0.248 psi and 0.265 psi for ales, equivalent to a fermentation temperature of 68° F.-72° F. In addition, an indication of head space pressure can be provided such that vaporization of the cooling medium is detected and displayed, indicating thermal activity inside the medium.

In accordance with a further aspect of the present disclosure, a cooling coil is utilized for the interior bottom of the fermentation tank, replacing a second cooling jacket used for aging of lagers. This cooling coil improves homogenization by preventing beer separation due to gravity, density, or temperature differences, or any combination of the forgoing, when yeasts are predominately dormant or not producing the $CO_2$ required for natural agitation. The coil may also be used for heating of the interior bottom of the fermentation tank if the vaporizing refrigerant is replaced, instead, with a condensing working gas.

The temperature set-point of the coil can be varied during the fermentation cycle, including cold crashing of beer, and is often a different value than the desired temperature of the fermentation tank or the temperature set-point of the elevated cooling jacket. This difference creates thermal gradients inside the tank, with the size of the gradient determined by the desired radius and temperature difference of the localized thermal volume surrounding the heating or cooling coil. These gradients, in turn, help to create movement of the medium through exploitation of the density differences of beer as a function of its local temperature—as a general principle, less dense, warmer fluid rises and more-dense, cooler fluid falls in the presence of gravity.

Figure 12:
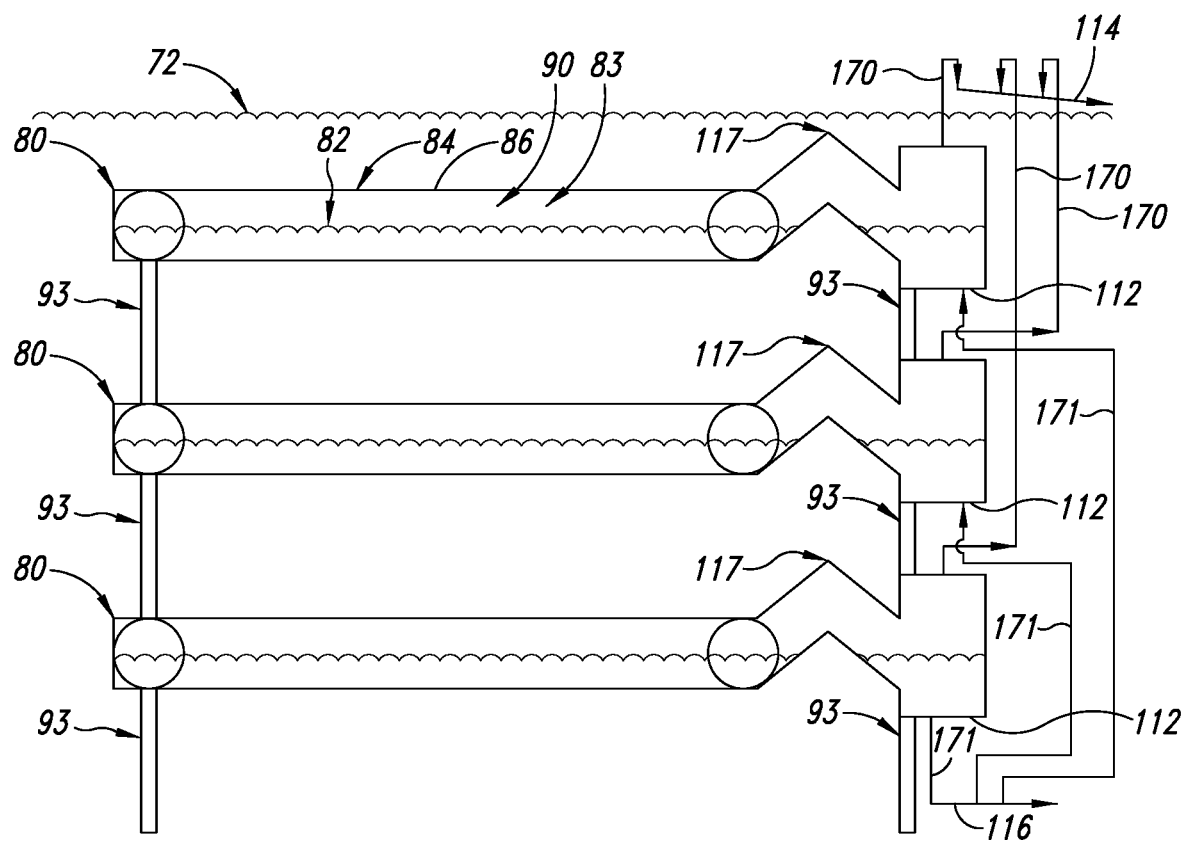
FIG. 12 is a side elevation cross-sectional illustration of a refrigerant reservoir formed in accordance with an alternative implementation of the apparatus of FIG. 8.

FIG. 12, which is described in more detail below, illustrates another aspect of the present disclosure, as cooling coil sections may be held at different vapor pressures without the use of multiple pressure regulators and with utilization of only a single vacuum source. Instead, the configuration of vertical piping 170 connecting the coil sections is varied to create a deliberate pressure drop between reservoirs. A longer pipe length or the addition of pipe fittings creates greater resistance to flow for the vaporizing refrigerant as it moves from a given refrigerant reservoir to the vacuum source. This resistance, in turn, creates different vapor pressures in the horizontal coil sections.

FIG. 12 illustrates an alternative implementation of the apparatus of FIG. 8 where refrigerant vapor streams are routed via vertical piping 170 to be brought together for collection above and outside the vessel or container. The diameter of the vertical piping 170 that routes the vapor streams can be smaller than the diameter of the horizontal tubes that form the respective reservoir sections 80, which increases the velocity of escaping refrigerant vapor streams. This helps to avoid condensation in the vertical piping 170, which would prevent vaporized refrigerant from escaping the cooling coil. In addition, there are fill and drain lines 171 that connect each manifold 112 to the common refrigerant fill and drain line 116. The orientation of the piping that forms the fill and drain lines 171 can be varied based upon the desired level of refrigerant 82 to be held in each manifold 112 after system drain.

For example, the addition of one 90 degree elbow in the piping between horizontal coil sections creates an added pressure drop of 0.0081 psi, assuming an ethanol refrigerant flow rate of 10 CFM at 0.3 psi and 38.7 degrees F. inside 4 ft long, 0.25 in diameter tubing. This pressure drop is equivalent to an approximate 0.8 degrees ° F. change in vaporization temperature inside the adjacent horizontal coils. A similar mechanical arrangement can be used to generate a pressure differential between horizontal sections of a heating coil utilizing a condensing working gas.

In accordance with another aspect of the present disclosure, cooling coil sections are held at a common vapor pressure using a single pressure regulator and a common vacuum source. However, the horizontal coil sections contain different types of refrigerant, with these refrigerants selected to vaporize at different temperatures and at a common vapor pressure. During operation, the flow of refrigerant vapor leaving the coil is, thus, multi-component and recovery is affected using a condenser and decanter, upstream of the vacuum pump. After decanting, refrigerant is returned to the designated horizontal coils by separate pumps, each designated for one type of condensed refrigerant. A similar mechanical configuration can be used for different types of condensing working gasses.

2. Use of a Condensing Working Gas or a Vaporizing Refrigerant to Indicate the Spatial Location of Heat Transfer In accordance with another aspect or implementation of the present disclosure, a temperature probe or site-glass, pressure, and vacuum gauge or other instrument is used to view or determine the condensing rate or vaporization rate of the fluid in the conduit. The vaporization rate is indicated by increased motion of the liquid refrigerant or by bubbles that form on the interior surface of the temperature control conduit or heat exchanger. These bubbles first form on the surface of the refrigerant reservoir, and then eventually detach and move upwards toward the head space. An operator, such as a brewer, can use the site-glasses or instruments to view the vaporization process and have visual or instrument-supplemented data to determine where heat is being generated by observing where the fluid motion occurs or where bubbles are being formed. The condensing rate is indicated by the presence of liquid due to condensation of a working gas.

Some brewers turn off their cooling systems because they have no accurate way of protecting against local thermal events only and do not want to risk thermal shock of the entire batch via activation of the cooling jacket. The present disclosure can also provide continued indication of local heat production through the unexpected presence of refrigerant at the vacuum pump or compressor. For example, indication may be used to signal the brewer to take corrective action to re-homogenize the tank. Similarly, the unexpected presence of a condensed working gas at the outlet of a heating coil indicates that a fermentation requires additional heat input to maintain temperature.

Additionally, the generation of localized thermal volumes surrounding working gas reservoirs or refrigerant reservoirs can provide useful information for troubleshooting of tank or vessel operating conditions. For example, if a vaporization apparatus is placed inside a tank or vessel and the apparatus thermal volumes are configured to allow a temperature differential of no more than 5 F from set-point, the presence of vaporized refrigerant indicates that at least some portion of the tank or vessel internal volume exceeds that temperature differential. This information is useful as it indicates that modifications to agitation speed, agitator type, baffle location, etc., should be affected to maintain the tank or vessel operating temperature at or below the desired set-point temperature.

In accordance with one aspect of the disclosure, working gas reservoirs or refrigerant reservoirs with site-glasses are placed in contact with the exterior of a tank or vessel. For a cooling coil, the visual observation of liquid refrigerant movement and bubble formation provides an indication of local heat transfer from the medium to the refrigerant. The relative magnitude of local heat transfer is illustrated by visual comparison of liquid refrigerant movement and bubble formation between horizontal sections. A similar comparison can be affected for working gas condensation by which the gas is visually observed condensing from a vapor to a liquid.

In accordance with another aspect of this disclosure a refrigerant vaporization apparatus can be configured with condensers mounted on the outlet lines of each horizontal reservoir section and between that section and a common vacuum source. During system operation, the liquid level in these condensers can be monitored. With known values for the size of the condenser and the density and latent heat of vaporization for a given refrigerant, a quantitative value for the heat transfer from the medium to each refrigerant coil section can be calculated.

For example, assuming an upright, cylindrical condenser of 12 in. diameter, a 1 in. change in level is equivalent to approximately 0.21 lb. of Ethanol. This equates to approximately 76 BTU's of heat transferred from the medium to the refrigerant reservoir. This same calculation can be used for a working gas condensation apparatus. In this instance, the volume of condensed liquid present in at each trap corresponds directly to the heat released from a reservoir to the medium.

In accordance with a further aspect of this disclosure is a refrigerant vaporization apparatus with pressure transmitters mounted on the outlet lines of each horizontal reservoir section. The sections are isolatable from the vacuum source via automated valves and, upon isolation, an increase in the horizontal section refrigerant vapor pressure indicates localized heat generation near that section. For an isolated working gas, a decrease in the horizontal section refrigerant vapor pressure indicates that the medium near that section required heat addition.

Figure 13:
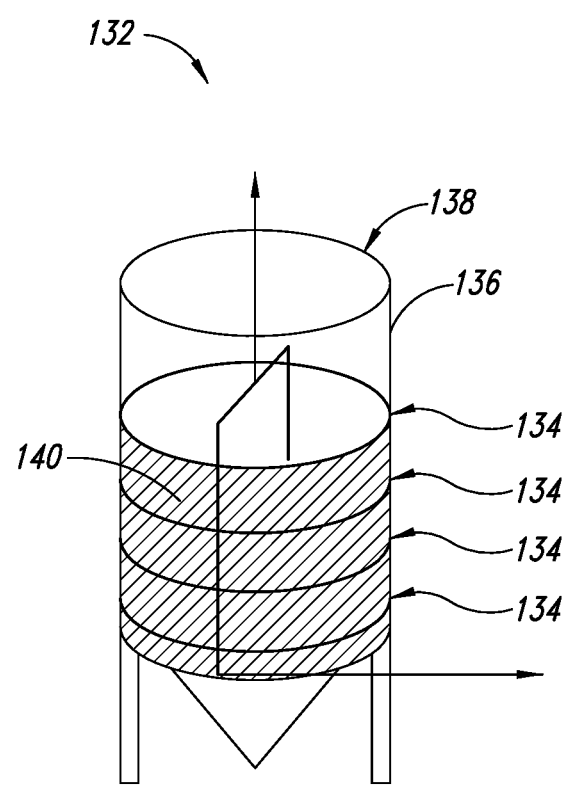
FIG. 13 is a pictorial representation of an alternative implementation of the present disclosure in which the coil apparatus is exterior to the container.

3. Use of a Buffer Medium to Improve the Consistency of Heat Transfer, where the Buffer Medium is in Thermal Contact with Both the Working Gas Reservoir or the Refrigerant Reservoir and the Medium FIG. 13 shows a system 132 employing a coil or series of connected coils 134 mounted on the exterior 136 of a container 138, such as a jacketed fermenter tank. A medium 140 is contained within the container 138. In this implementation, the coils 134 attached to the exterior 136 of the container 138 provide contact between a buffer medium and both the container 138 and the medium 140 in the container 138.

Sequentially, for a cooling coil, heat is conducted first from the medium to the wall of the tank or vessel, then through the wall to the buffer medium, then from the buffer medium to wall of the coil, and finally through the coil wall to the refrigerant. For a heating coil, this heat transfer process is reversed with heat flow beginning at the working gas and ending at the medium. Quantitatively, the coil spacing equation is modified to account for the added resistance of both the buffer medium and the buffer medium's enclosing surface:

$$V = I * R \text{ Electrical Analogy}$$

$$\Delta T = Q * R \text{ Heat Transfer Equation}$$

$$\frac{\Delta T}{L} = \frac{Q * R}{L} \text{ Divide by Length of Horizontal Section}$$

$$\frac{Q}{L} = \frac{\Delta T}{R * L} \text{ Rearrange}$$

L=Length of horizontal lattice section (m);
Q=Total heat transferred from medium to horizontal section per unit time (W);
R=Total resistance to heat transfer across the temperature differential per unit time (K/W); and
ΔT=Maximum temperature difference between medium and condensing working gas or vaporizing refrigerant (K).

$$\Delta T = T2 - T1 \text{ Temperature Differential } (K)$$

$$R = \left[ \frac{1}{H1*A1} + \frac{\ln\left(\frac{R2}{R1}\right)}{2*\pi*L*K1} + \frac{\ln\left(\frac{R4}{R2}\right)}{2*\pi*L*K2} + \right.$$

$$\left. \frac{\ln\left(\frac{R5}{R4}\right)}{2*\pi*L*K3} + \frac{1}{H2*A5} \right] \begin{array}{l} \text{Resistance to} \\ \text{Heat Transfer} \\ (K/W) \end{array}$$

$$R = \frac{1}{2*\pi*L} * \left( \frac{1}{H1*R1} + \frac{\ln\left(\frac{R2}{R1}\right)}{K1} + \right.$$

$$\left. \frac{\ln\left(\frac{R4}{R2}\right)}{K2} + \frac{\ln\left(\frac{R5}{R4}\right)}{K3} + \frac{1}{H2*R5} \right) \text{Substituting}$$

$$R*L = \frac{1}{2*\pi} * \left( \frac{1}{H1*R1} + \frac{\ln\left(\frac{R2}{R1}\right)}{K1} + \right.$$

$$\left. \frac{\ln\left(\frac{R4}{R2}\right)}{K2} + \frac{\ln\left(\frac{R5}{R4}\right)}{K3} + \frac{1}{H2*R5} \right) \begin{array}{l} \text{Resistance} \\ \text{to Heat} \\ \text{Transfer} \\ \text{Across} \\ \text{Length} \\ (K*m/W) \end{array}$$

$$Q = J*(\pi*R3^2*L - \pi*R5^2*L) \begin{array}{l} \text{Heat Generated by Medium} \\ \text{per Unit Time for a} \\ \text{Horizontal Section } (W) \end{array}$$

$$\frac{Q}{L} = J*\pi*(R3^2 - R5^2) \begin{array}{l} \text{Heat Generated by Medium} \\ \text{per Length of Horizontal} \\ \text{Section per Unit Time } (W/m) \end{array}$$

A5=Surface area of exterior wall of the buffer medium enclosing surface (m$^2$)
H1=Working gas or refrigerant heat transfer coefficient, including boundary layer effects (W/m$^2$*K);
H2=Medium heat transfer coefficient, including boundary layer effects (W/m$^2$*K);
J=Maximum heat generated or lost by medium per unit volume per unit time (W/m$^3$);
K1=Thermal conductivity of lattice material of construction (W/m*K);
K2=Thermal conductivity of buffer medium (W/m*K);
K3=Thermal conductivity of buffer medium enclosing surface material of construction (W/m*K);
R1=Radius from center of horizontal lattice section to inside of lattice wall (m);
R2=Radius from center of horizontal lattice section to outside of lattice wall (m);
R3=Radius from center of horizontal lattice section to outside of medium volume (m);
R4=Radius from center of horizontal lattice section to outside of buffer medium (m);
R5=Radius from center of horizontal lattice section to outside of buffer medium enclosing surface (m);
T1=Temperature at working gas or liquid-vapor refrigerant interface (K); and T2=Temperature of medium at outer edge of medium volume (K).

$$\frac{Q}{L} * (R*L) - \Delta T = 0 \quad \text{The Rearranged Heat Transfer Equation Set Equal to Zero}$$

$$J * \pi * (R3^2 - R5^2) * \frac{1}{2*\pi} *$$

$$\left( \frac{1}{H1*R1} + \frac{\ln\left(\frac{R2}{R1}\right)}{K1} + \frac{\ln\left(\frac{R4}{R2}\right)}{K2} + \frac{\ln\left(\frac{R5}{R4}\right)}{K3} + \frac{1}{H2*R5} \right) -$$

$$(T2 - T1) = 0 \text{ Substituting}$$

$$R3 = \sqrt{\frac{\frac{1}{J*\pi} * (T2-T1) *}{\frac{1}{2*\pi} * \left( \frac{1}{H1*R1} + \frac{\ln\left(\frac{R2}{R1}\right)}{K1} + \frac{\ln\left(\frac{R4}{R2}\right)}{K2} + \frac{\ln\left(\frac{R5}{R4}\right)}{K3} + \frac{1}{H2*R5} \right)} + R5^2} \quad \text{Setting Equal to } R3$$

Note that the resistance to heat transfer of the buffer medium is calculated using its thermal conductivity, K2 and the inner radius and outer radius of the buffer medium, R2 and R4, respectively. It may be considered that the buffer medium is a moving fluid, such as water in the turbulent regime. In this instance, use of the buffer medium heat transfer coefficient H with units of W/m²K may be more appropriate, with this value accounting for boundary layer effects at both the coil outer surface and the inner surface of the buffer enclosure. For simplicity of the derivation, these effects have been combined into the value of K2, with units of W/m*K per unit length of horizontal section.

Figure 14:
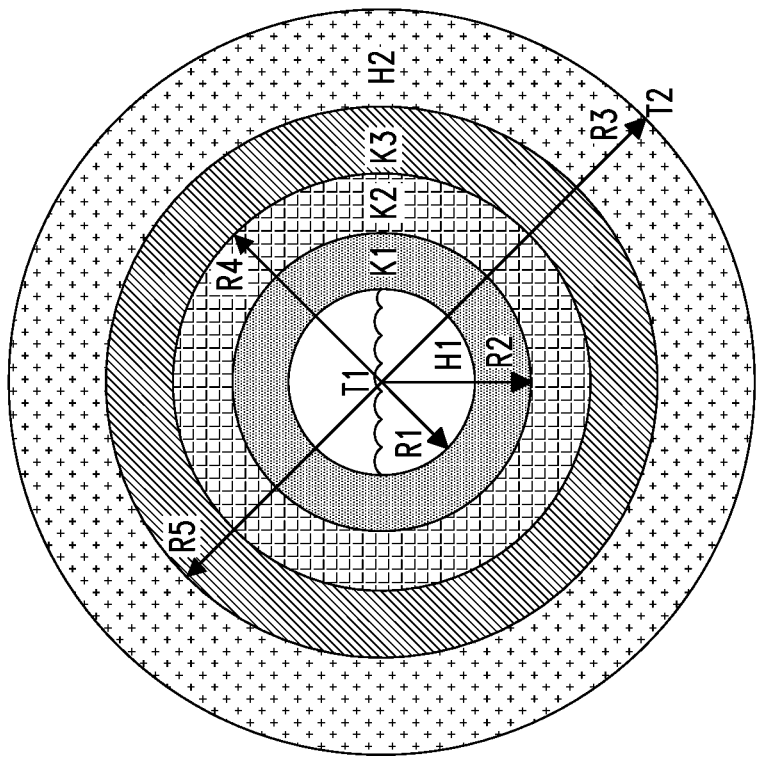
FIG. 14 is a cross-sectional illustration of radial heat transfer along the length of a horizontal lattice section.

Referring to FIG. 14, for a given horizontal lattice section, the mechanical design must be capable of the desired heat transfer rate, subject to the added thermal resistances. When a working gas reservoir or refrigerant reservoir is placed external to a tank or vessel, the air between adjacent coils may be considered the buffer medium and the tank or vessel wall the buffer medium enclosing surface. Ideally, however, a buffer medium will transport heat with minimal resistance and is of a material of construction favorable to the desired heat transfer rate. The material of construction of the buffer medium enclosure must be compatible with the medium as well.

The buffer medium may also act to extend the radius of the localized thermal volume, reducing the temperature gradient between adjacent working gas or refrigerant coils. This is useful for fermentation tanks, where it is desirable to hold a constant temperature across the profile of the tank exterior, such as to provide a constant temperature environment at the outer boundary of the medium and to help prevent thermal shock due to activation of the temperature control system.

In accordance with another aspect of the present disclosure, the apparatus shown in FIG. 13 may be placed inside the tank or vessel. In this instance, the buffer medium is in thermal contact with both the working fluid or refrigerant coils and the medium. The localized thermal volumes exterior to the reservoirs are then extended beyond the thermal volumes normally created if the coils were submerged without the buffer medium and its enclosure.

For example, if 1 in. inner diameter, 1.15 in. outer diameter stainless steel, ethanol refrigerant vaporization coils are submerged in a tank or vessel with a coil centerline to centerline spacing is approximately 8.75 in., the calculated temperature gradient at the midpoint between adjacent coils is approximately 8 degrees F. If the coil centerline spacing is maintained, but an aluminum buffer medium is used with a stainless steel, buffer medium enclosure of 1.5 in. inner diameter, 1.625 in. outer diameter, the calculated temperature gradient at the midpoint between adjacent coils decreases to approximately 6.35 degrees F.

4. Generation of Currents Inside the Vaporizing Refrigerant to Improve Heat Transfer by Variation of Vapor Pressure In accordance with still yet a further aspect of the present disclosure, the cooling coil mechanical design provides for agitation of cooling fluid inside the cooling coil tubes themselves, further improving heat transfer from the cooling liquid in the coil to the vapor interface. Agitation results from the mechanical design, by which a common refrigerant vapor space is linked to at least two ends of a liquid refrigerant filled coil. As the liquid refrigerant vaporizes due to vacuum, the vapor generated moves toward the common vapor space, and this movement causes agitation of the refrigerant liquid volume between the vapor source and common headspace. However, because the liquid refrigerant volume is connected to a common headspace at more than one location, vapor generation causes part of the liquid volume to move in a direction opposite that of which the vapor is traveling, and this portion of liquid can move to fill part of the common headspace. The result is that part of the liquid refrigerant in the coil then moves relative to the coil interior surface. Liquid refrigerant movement promotes uptake of refrigerant vapor, generated on the interior surface of the coil, into the refrigerant liquid, and thereby improves heat transfer from the medium external to the coil to the refrigerant contained therein. For example, assuming an ethanol refrigerant, a vacuum level between 0.248 psi and 0.265 psi would be required, equivalent to a fermentation temperature of 68° F.-72° F. for beer ales.

Figure 15:
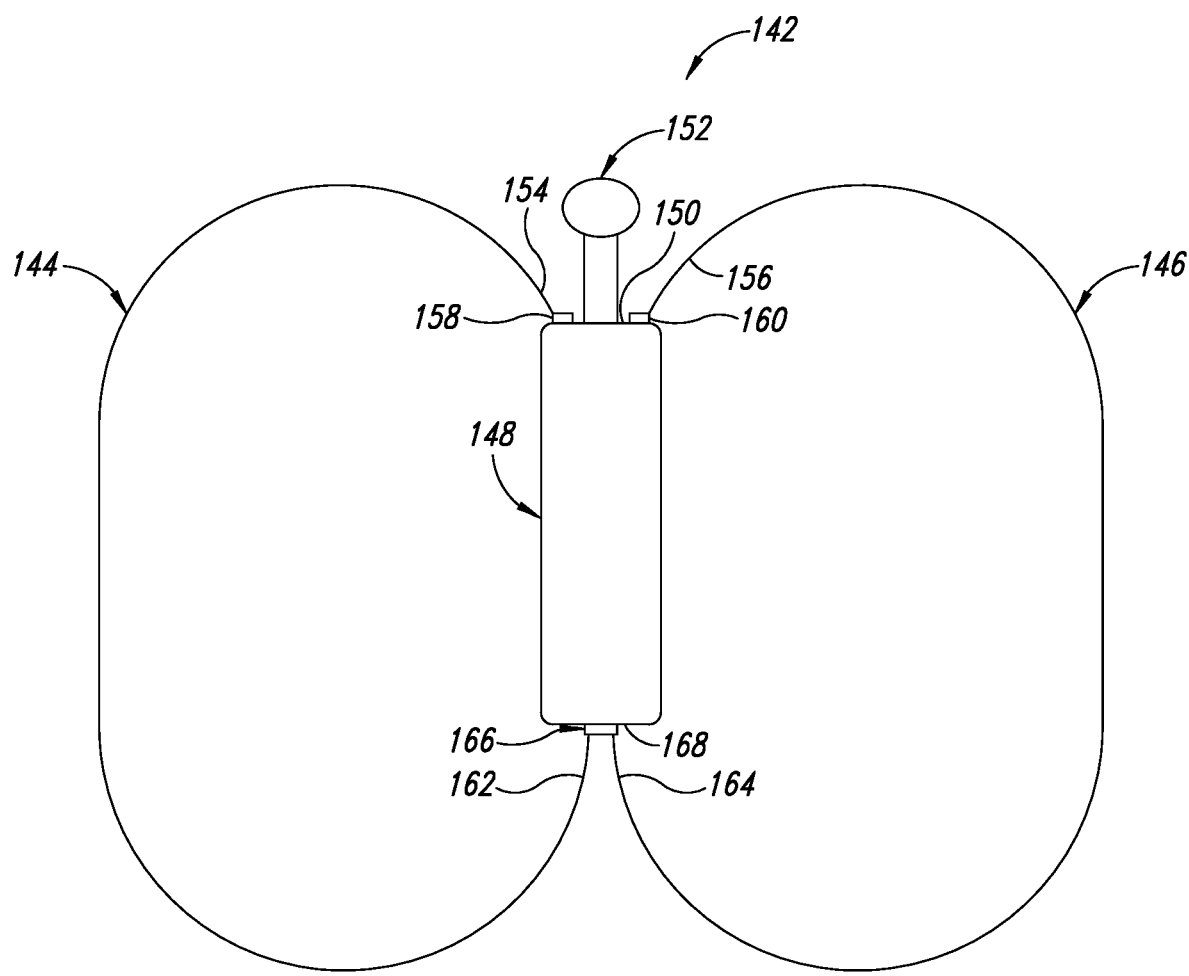
FIG. 15 is an illustration of an oscillatory vacuum coil and reservoir design in which fluid in the coils will oscillate due to pressure differentials in accordance with another implementation of the present disclosure.

The foregoing is illustrated in FIG. 15, which shows a vacuum coil and reservoir system 142 consisting of two coils, a first coil 144 and a second coil 146, coupled to a common vacuum coil reservoir 148, at the top 150 of which is a vacuum equalization line 152. Each of the first and second coils 144, 146 have a first end 154, 156 respectively coupled to individual first and second ports 158, 160 at the empty head space at the top 150 of the reservoir 148. In addition, each of the first and second coils 144, 146 have a second end 162, 164 respectively coupled to a common port 166 at the second end 168 or the liquid full part of the reservoir 148. Essentially, when a vacuum is enabled, the liquid in the coils 144, 146 begins to oscillate relative to the two connection ports 158, 160 at the top 150 of the reservoir 148. When observed through clear coil tubing, it appears that the liquid tries to escape through one side of the top connection ports 158, 160, then gets dragged back and tries to escape then through the other side of the top connection, but is never successful in escaping through either connection. This would be the observed oscillatory motion. The reservoir is mechanically configured to replenish the liquid refrigerant vaporized, holding constant the level of the liquid refrigerant in the coil, relative to the starting and ending positions of the oscillations 5. Pre-Heating of the Refrigerant When refilling the system with refrigerant, the refrigerant can be heated above the current temperature of the medium. Once introduced to the refrigerant reservoirs, heat is conducted through the reservoir walls to the medium as the refrigerant cools, warming the medium. The refrigerant is then vaporized when cooling is desired. Thus, both heating and vaporization cooling can be affected by the same refrigerant vaporization apparatus.

Figure 16:
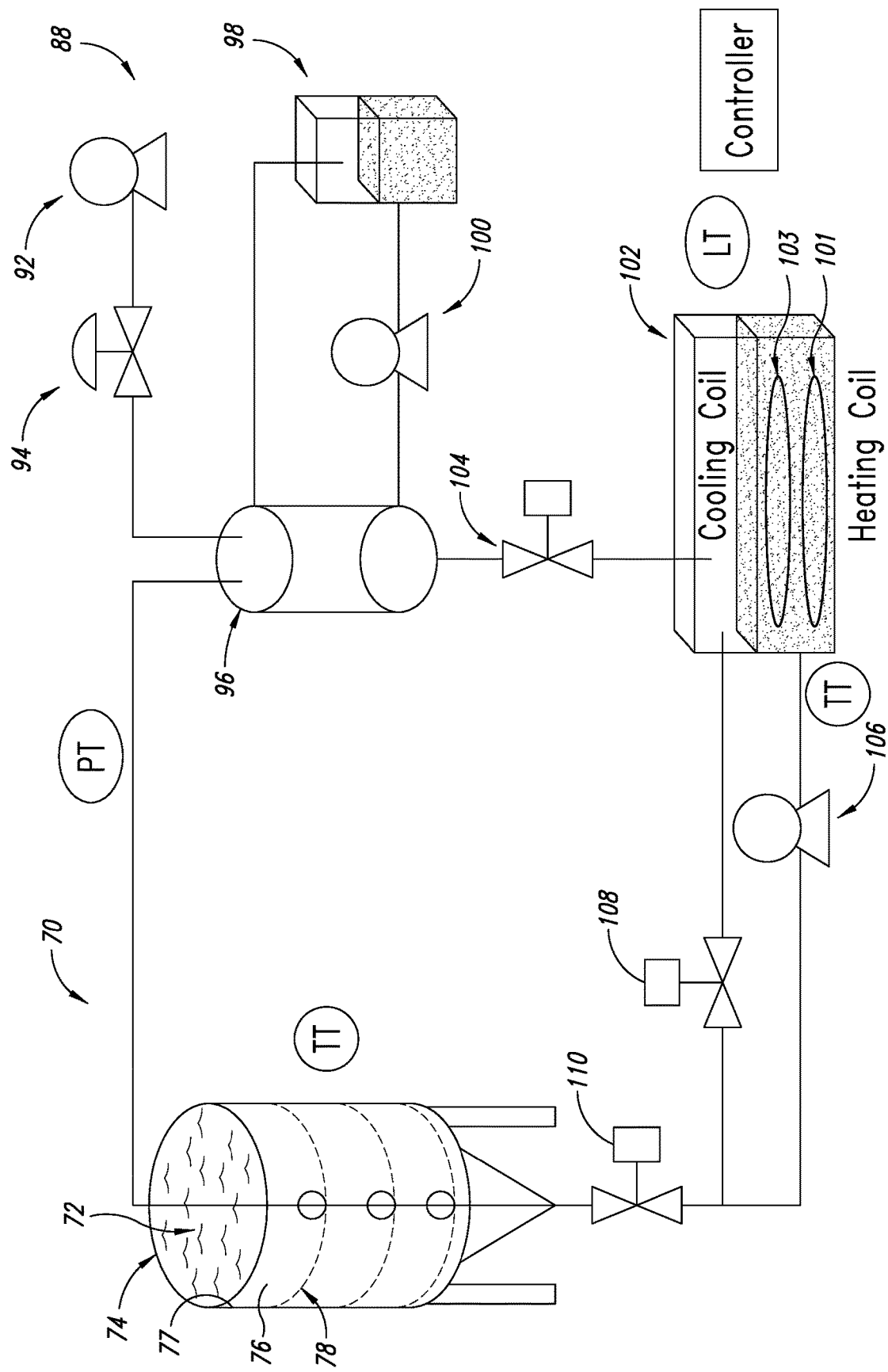
FIG. 16 is an illustration of a system formed in accordance with a representative implementation of the present disclosure in which refrigerant is pre-heated before refill of the refrigerant reservoirs.

FIG. 16, which an adaptation of FIG. 7 described above shows a system 70 with a vacuum source 92, fermentation tank 74, fermentation tank temperature transmitter TT, refrigerant reservoirs 78, refrigerant supply pump 106, refrigerant tank 102, and refrigerant supply temperature transmitter TT. The temperature of the refrigerant in the refrigerant tank 102 is regulated using a heating coil 101 and cooling coil 103. Heating of the medium is accomplished by adjusting the set-point temperature of the refrigerant above the current temperature of the medium and then supplying this refrigerant to the refrigerant reservoirs.

6. Heating and Cooling Using a Heat Transfer Medium

Temperature control of the medium can be accomplished by continuous flow of a heat transfer fluid through either the working gas apparatus or refrigerant apparatus. However, the temperature profile of the heat transfer fluid will vary across the coil reservoirs, proportional to the rate and special location of heat transfer to/from the medium. This temperature gradient does not exist with either a condensing working gas or a vaporizing refrigerant, as both types of phase change provide a constant temperature heat source or sink across the same coil. However, for applications where a variation in coil temperature is acceptable, heating or cooling via flow of a heat transfer fluid may be a viable alternative to heating via working gas condensation or cooling via refrigerant vaporization. In this instance, coil spacing of either the heating or cooling coil is defined by the same equation as the condensing working gas or vaporizing refrigerant method, so as to best approximate the performance of condensing working gas or vaporizing refrigerant.

To affect both heating and cooling, without the use of either a condensing working gas or vaporizing refrigerant, temperature variation across the coil is best minimized if the flow of heat transfer medium is high and if the flow can be characterized in the turbulent regime. The greater the flowrate of a volume of heat transfer medium, at constant heat flux, the less that volume will warm or cool over a fixed length of coil section, as it has reduced time to absorb or release heat. Turbulence, inside the coil sections, can increase the heat transfer coefficient of the heat transfer media such that the coefficient approaches that of a condensing working gas or a vaporizing refrigerant.

Figure 17:
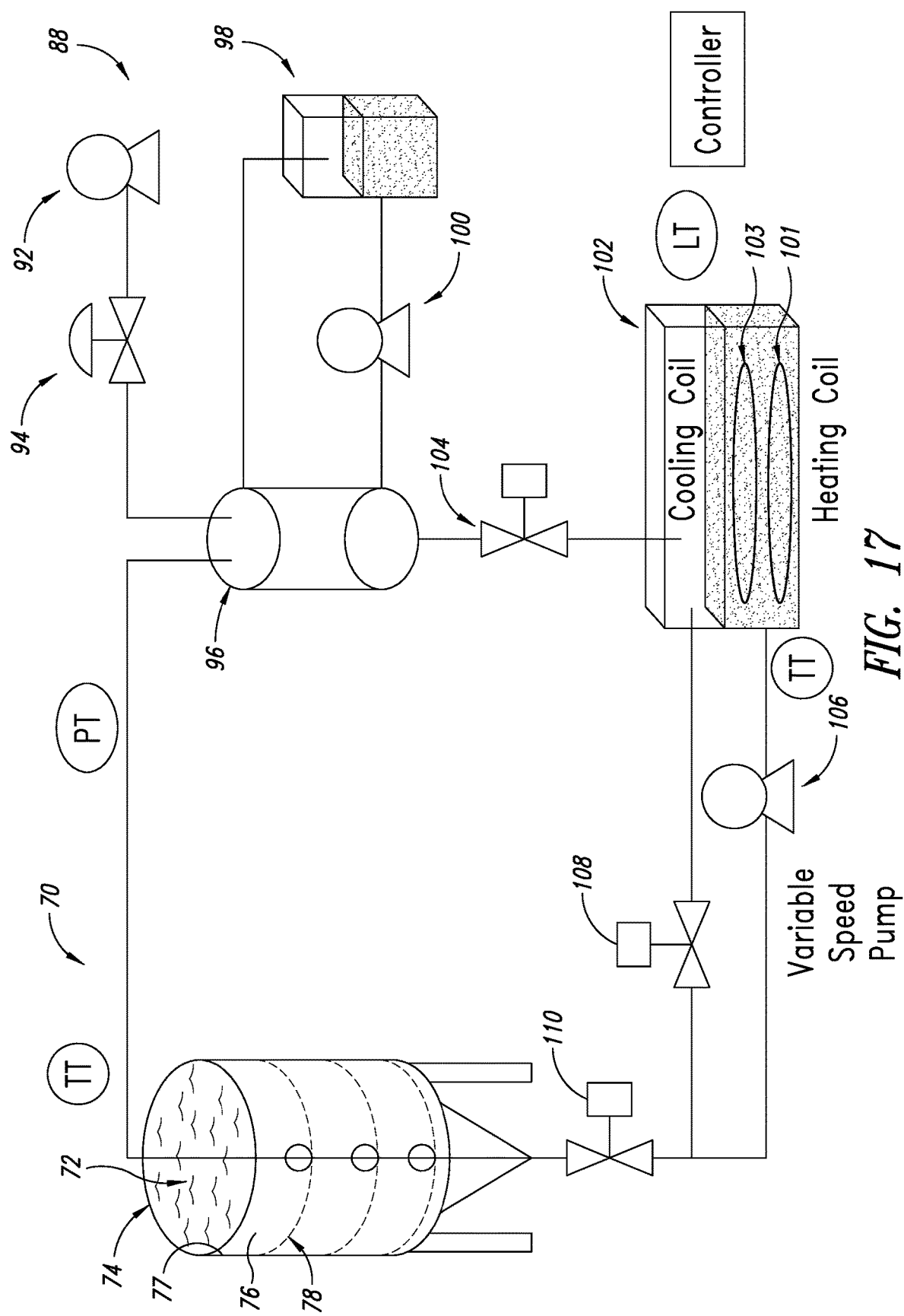
FIG. 17 is an illustration of a system formed in accordance with the present disclosure in which a heat transfer medium is circulated through the reservoirs and the flow rate is varied based upon measured temperatures.

For example, FIG. 17, which is essentially FIG. 16 modified, shows a refrigerant vaporization apparatus with a heat transfer medium inlet and outlet. Heat transfer medium flow rate can be adjusted using a variable speed pump 106, and inlet temperature is controlled using a heating coil 101, a cooling coil 103, and temperature indication TT on the heat transfer medium supply tank 102, and outlet temperature is monitored using temperature indication TT in the piping connecting the refrigerant reservoirs 78 and the condenser 96. The heat transfer medium temperature in the connecting piping is monitored and the speed of the pump 106 varied to ensure that the temperature loss or rise across the coil does not exceed a set-point. This acts best to preserve the distribution of the localized thermal volumes created by the mechanical design of the refrigerant apparatus by holding the exterior temperature of the coil at or near a constant value.

In accordance with a further aspect of this disclosure, the heat transfer medium is pumped in parallel through the horizontal coils of either a working gas apparatus or a vaporization apparatus with the objective of reducing the temperature rise across each coil. Coil temperature at each outlet is monitored and the heat transfer medium flow rates to each horizontal section are adjusted, with the aim of approximating the zero-temperature change condition across coil.

7. Condensation of a Working Fluid to Provide Heating

The refrigerant vaporization apparatus provides for process cooling of a medium utilizing a minimum temperature gradient. The mechanical design of the refrigerant vaporization apparatus creates a volume of medium thermal coverage surrounding the individual refrigerant reservoirs, and these reservoirs are configured such that the respective boundaries of thermal coverage are at least contiguous. The designer of the refrigerant vaporization apparatus then chooses a spacing between adjacent refrigerant reservoirs as a function of the allowable temperature variation inside the medium to be cooled. When operational, the refrigerant vaporization apparatus effectively places an upper bound on the allowable temperature of the medium.

If the vaporizing refrigerant inside the apparatus is replaced with a condensing working gas, the apparatus now functions in reverse, heating the medium with a minimum temperature gradient. The volumes of medium thermal coverage are maintained in both magnitude and special location, and the volumes serve also to place a lower bound on the allowable temperature of the medium. The equation to calculate ideal coil spacing for the working gas condensation apparatus is identical to that of the refrigerant vaporization apparatus, per the example derivation below:

$$V = I * R \text{ Electrical Analogy}$$

$$\Delta T = Q * R \text{ Heat Transfer Equation}$$

$$\frac{\Delta T}{L} = \frac{Q * R}{L} \text{ Divide by Length of Horizontal Section}$$

$$\frac{Q}{L} = \frac{\Delta T}{R * L} \text{ Rearrange}$$

L=Length of horizontal lattice section (m);
Q=Total heat transferred from medium to horizontal section per unit time (W);
R=Total resistance to heat transfer across the temperature differential per unit time (K/W); and
$\Delta T$=Maximum temperature difference between medium and condensing working gas (K).

$$\Delta T = T2 - T1 \text{ Temperature Differential } (K)$$

$$R = \left( \frac{1}{H1 * A1} + \frac{\ln\left(\frac{R2}{R1}\right)}{2 * \pi * L * K1} + \frac{1}{H2 * A2} \right) \begin{array}{l} \text{Resistance to} \\ \text{Heat Transfer} \\ (K/W) \end{array}$$

$$R = \frac{1}{2 * \pi * L} * \left( \frac{1}{H1 * R1} + \frac{\ln\left(\frac{R2}{R1}\right)}{K1} + \frac{1}{H2 * R2} \right) \text{Substituting}$$

$$R * L = \frac{1}{2 * \pi} * \left( \frac{1}{H1 * R1} + \frac{\ln\left(\frac{R2}{R1}\right)}{K1} + \frac{1}{H2 * R2} \right) \begin{array}{l} \text{Resistance} \\ \text{to Heat} \\ \text{Transfer} \\ \text{Across} \\ \text{Length} \\ (K * m/W) \end{array}$$

-continued $$Q = J * \left(\pi * R3^2 * L - \pi * R2^2 * L\right) \quad \begin{array}{l}\text{Heat Generated by Medium}\\ \text{per Unit Time for a}\\ \text{Horizontal Section } (W)\end{array}$$

$$\frac{Q}{L} = J * \pi * \left(R3^2 - R2^2\right) \quad \begin{array}{l}\text{Heat Generated by Medium}\\ \text{per Length of Horizontal}\\ \text{Section per Unit Time } (W/m)\end{array}$$

A2=Surface area of exterior wall of horizontal lattice section (m²);
H1=Condensing working gas heat transfer coefficient, including boundary layer effects (W/m²*K);
H2=Medium heat transfer coefficient, including boundary layer effects (W/m²*K);
J=Maximum heat generated by medium per unit volume per unit time (W/m³);
K1=Thermal conductivity of lattice material of construction (W/m*K);
R1=Radius from center of horizontal lattice section to inside of lattice wall (m);
R2=Radius from center of horizontal lattice section to outside of lattice wall (m);
R3=Radius from center of horizontal lattice section to outside of medium volume (m);
T1=Temperature of condensing working gas (K); and
T2=Temperature of medium at outer edge of medium volume (K).

$$\frac{Q}{L} * (R * L) - \Delta T = 0 \quad \begin{array}{l}\text{The Rearranged Heat Transfer}\\ \text{Equation Set Equal to Zero}\end{array}$$

$$J * \pi * \left(R3^2 - R2^2\right) * \frac{1}{2*\pi} *$$

$$\left(\frac{1}{H1*R1} + \frac{\ln\left(\frac{R2}{R1}\right)}{K1} + \frac{1}{H2*R2}\right) - (T2 - T1) = 0 \text{ Substituting}$$

$$R3 = \sqrt{\frac{\frac{1}{J*\pi}*(T2-T1)*}{\frac{1}{2*\pi}*\left(\frac{1}{H1*R1} + \frac{\ln\left(\frac{R2}{R1}\right)}{K1} + \frac{1}{H2*R2}\right)} + R2^2} \quad \begin{array}{l}\text{Setting}\\ \text{Equal}\\ \text{to } R3\end{array}$$

Note that the temperature at the center of the working gas reservoir, T1, is now less than the temperature at the outer edge of the volume of medium thermal coverage, T2, and the heat generated by the medium per unit volume per unit time, J, now carries a negative value, indicating that the medium is losing heat per unit volume per unit time. The changes in sign for both the temperature differential, ΔT, and heat production, J, cancel out and the expression inside the square root term always remains positive, providing a real solution for value R3.

Figure 19:
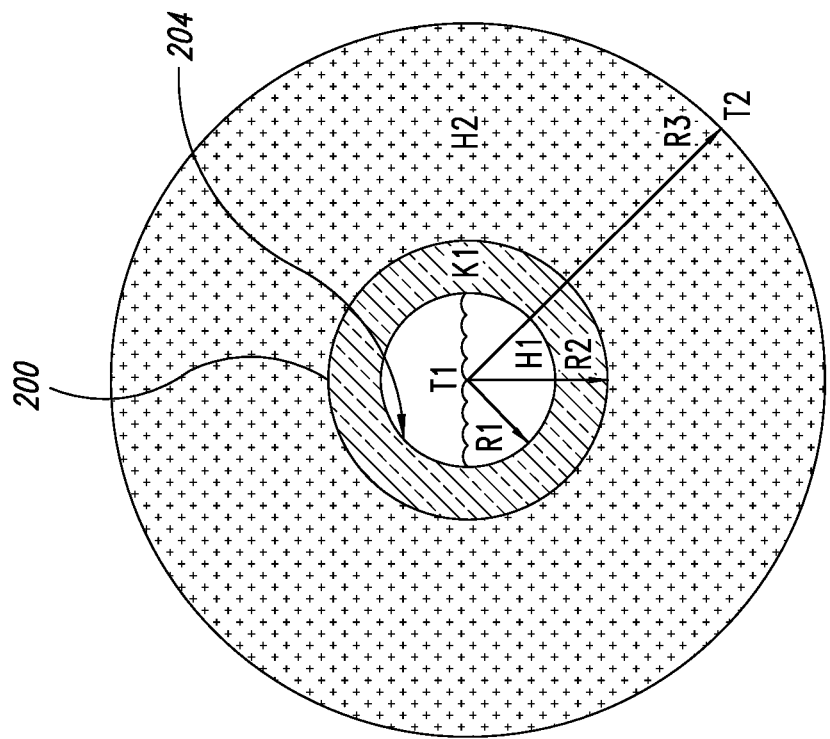
FIG. 19 is a cross-sectional illustration of radial heat transfer along the length of the horizontal lattice section of FIG. 18.
Figure 18:
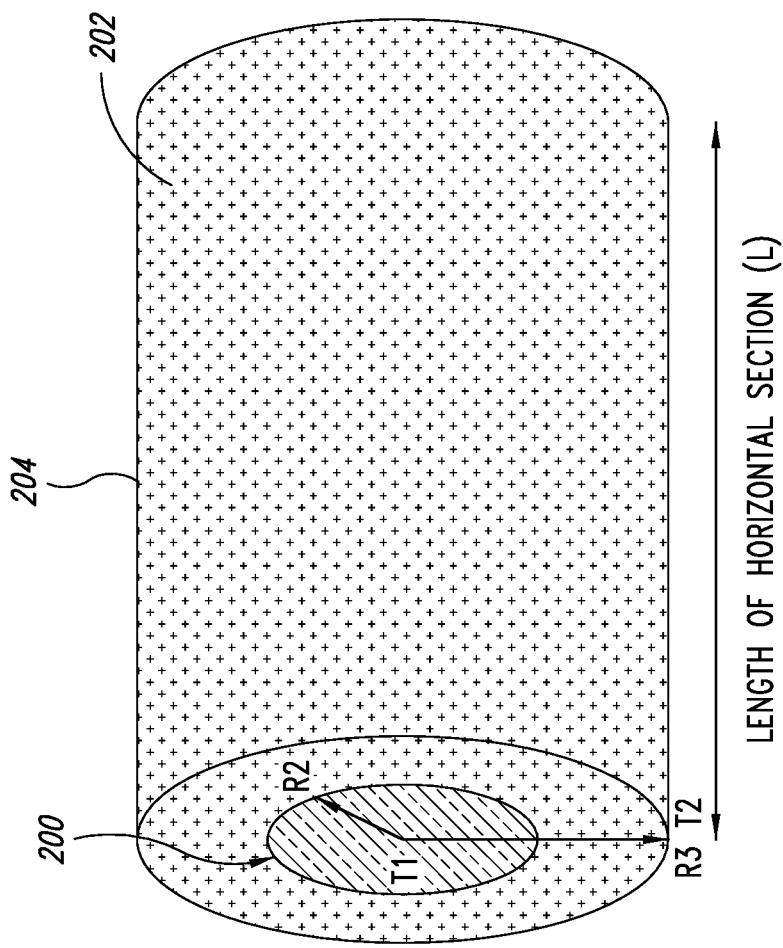
FIG. 18 is an illustration of radial heat transfer along a length of the horizontal lattice section in accordance with the present disclosure.

Referring to FIGS. 18 and 19, for a given horizontal lattice tube section 200, the mechanical design must be capable of supplying the maximum heat required by a medium volume 202 surrounding that horizontal lattice section 200 that has an outside boundary 204. This volume 202 can be approximated by assuming a cylindrical shape surrounding the horizontal lattice section 200 with a radius R3, the combination of the distance from lattice centerline to the tube exterior R2 and the distance from the lattice exterior at R2 to a centerline between adjacent lattices. The volume of the mechanical lattice is then subtracted from the total volume of the medium filled container to calculate the volume of the heat requiring medium.

R1 is the inner radius of a lattice tube and should be selected in coordination with the horizontal length L of horizontal lattice sections 200 to provide sufficient surface area for heat transfer from the lattice structure to the medium. As with the refrigerant vaporization apparatus, design consideration must be given to pressure drop in a lattice headspace during system operation. Unlike the refrigerant vaporization apparatus, though, there should be minimal liquid level present in a horizontal lattice tube section 200, as any condensed working gas must be removed quickly to maintain an interior lattice tube surface free of obstructions which may reduce the condensation rate.

Also, as with the refrigerant vaporization apparatus, the design and mathematical methodology of the horizontal lattice tube sections can be adapted for use outside of a container. Consideration must be given to the additional heat transfer resistance created by the container wall and medium surrounding the horizontal sections (e.g., air). These resistances can be accounted for via reduced values for h1, h2, or k1 in the spacing equation or through a more rigorous treatment of heat transfer resistances as shown in the modified spacing equation found in implementation 3 of the current disclosure. It is often most practical to modify the resistance terms h1, h2, or k1 so as to reflect empirical data, however, keeping computation to a minimum.

Ideal spacing of the horizontal lattice tube sections for the working gas condensing apparatus remains as calculated by right angle geometry for the refrigerant vaporization apparatus. FIGS. 20, 21, 22 show alternative geometric configurations that can increase spacing between lattice sections, though these configurations risk that part of the medium may fall below the design temperature range due to insufficient heating. FIG. 20 is a cross-sectional illustration of multiple heating volumes with minimal coverage, FIG. 21 is a cross-sectional illustration of multiple heating volumes with partial coverage, and FIG. 22 is a cross-sectional illustration of multiple heating volumes with complete coverage.

Figures 23, 24:
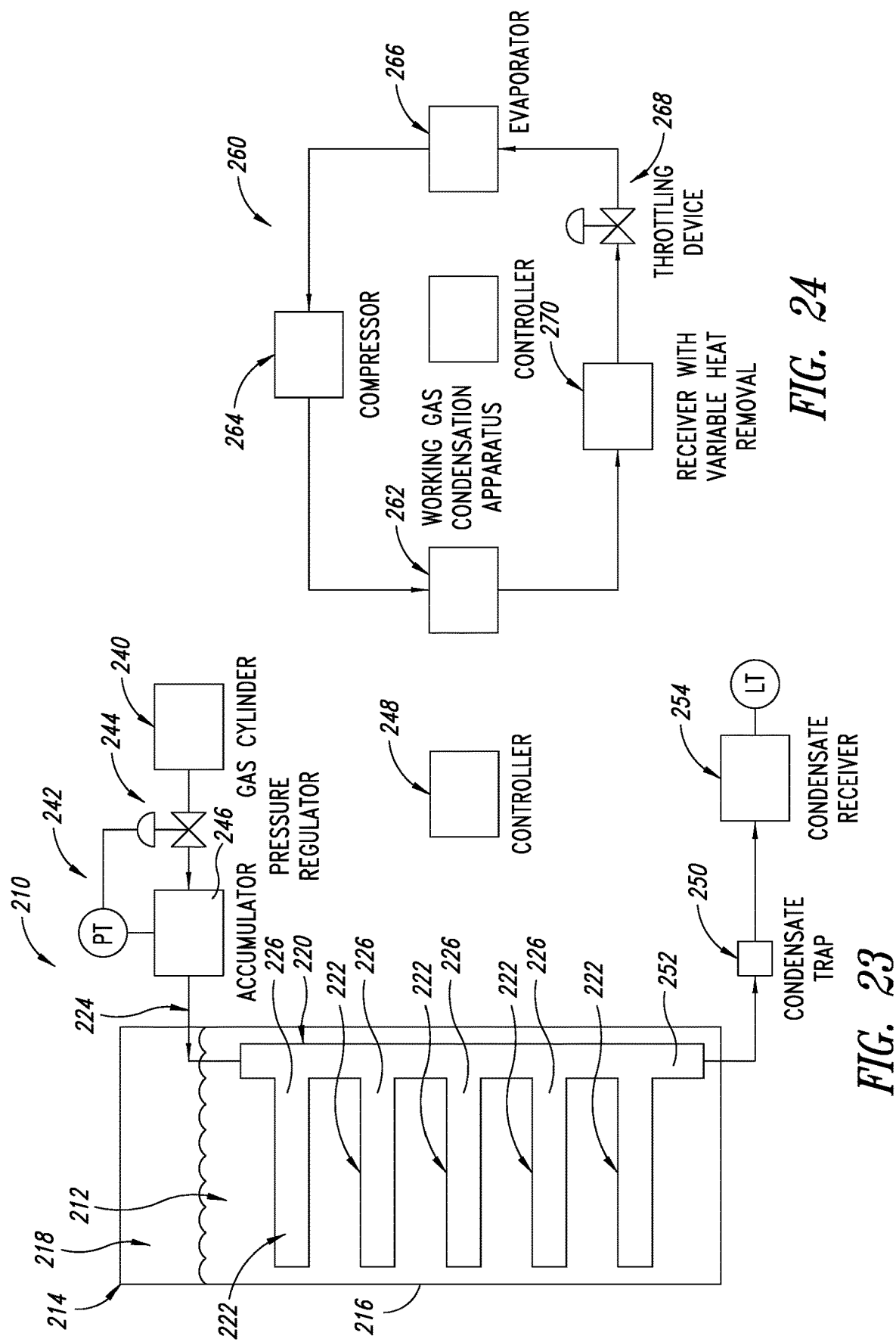
FIG. 23 is an illustration of a system formed in accordance with a representative implementation of the present disclosure.
FIG. 24 is an illustration of a system formed in accordance with an alternative implementation of the system in FIG. 23.

FIG. 23 illustrates a system 210 to control the temperature of a medium 212 by working gas condensation. In this representative implementation the system includes a container 214 having an exterior 216 and an interior 218. At least one working gas reservoir 220 is associated with the container 214, the working gas reservoir 220 including at least one reservoir section 222 structured to hold working gas 224 in an internal reservoir space 226. In this implementation, there are a plurality of reservoir sections 222 as shown more clearly in FIGS. 25 and 26, each reservoir section 222 having a wall 228 with an exterior surface 230 structured to be thermally coupled with the volume of the medium 212 in the container 214 and to provide thermal change to the volume of the medium 212 in container 214 and thereby provide a volume of medium thermal coverage in the container 214 as described above in connection with FIGS. 18 and 22 and to be described more fully below.

Each of the reservoir sections 222 has its respective internal reservoir space 226 in fluid communication with at least one other internal reservoir space 226 of an adjacent reservoir section 222, and the plurality of reservoir sections 222 are arranged in spaced relationship to adjacent reservoir sections 222 with the respective volumes of medium thermal coverage having the respective boundaries of thermal coverage to be at least contiguous.

The system 210 further includes a gas cylinder 240 for supply of working gas to the reservoir sections 222 and a working gas pressure apparatus 242 to provide regulation of working gas pressure in the reservoir sections 222. The reservoir sections 222 are each configured to form a vapor space 232 in each reservoir section 222 in response to receiving working gas 224 and in response to the working gas pressure apparatus 242 regulation of the pressure of the working gas 224 to enable working gas condensation at or near a selected temperature of the volume of medium thermal coverage (for example 202 above) for the volume of the medium 212 in the container 214 that is thermally coupled to the respective reservoir section 222.

It is to be understood that the working gas pressure apparatus 242 can be implemented with readily available commercial equipment and hence will not be described in detail herein. Briefly, the working gas pressure apparatus 242 includes the gas cylinder 240 in fluid communication with the working gas reservoir 220. Ideally, both a pressure regulator 244 and an accumulator 246 are positioned between the gas cylinder 240 and the working gas reservoir 220. Control of the pressure regulator 244 can be performed manually or, more preferably, by automated controls in a controller 248 that utilizes sensors and a computer processor to process signals from the sensors and transmit control signals to the pressure regulator 244 in response to the sensor signals.

In the implementation of FIG. 23, a condensate trap 250 is provided to remove the condensed working gas, such as R-134a. The condensate trap 250 is in fluid communication with the working gas reservoir 220 via an exit tube 252, which may be gravity fed, to provide either a continuous or continual supply of condensed working gas to a condensate receiver tank 254. Ideally, the condensate receiver tank 254 has a level transmitter LT that senses and transmits an indication of the volume of condensate in the condensate receiver tank 254 to avoid placing backpressure that may impede proper function of the condensate trap 250. The pressure in the working gas reservoir 220 is maintained at set-point pressure by the working gas pressure apparatus 242 and condensed working gas is removed by gravity drain to the condensate trap 250.

FIG. 24 is an illustration of an alternative implementation of a system 260 to the system 210 shown in FIG. 23. Working gas is supplied to the working gas condensation apparatus 262 continuously through use of a compressor 264, evaporator 266, throttling device 268, receiver with variable heat removal 270, and controller 248. This implementation closely mirrors the functionality of a traditional refrigeration system; however, the refrigerant is replaced by a working gas. In this implementation, the working gas is compressed by the compressor 264, condensed in the working gas condensation apparatus 262 and receiver 270, expanded through the throttling device 268, evaporated in the evaporator 266, then returned to the compressor 264. The controller 248 is provided for system automation.

The receiver 270 is capable of variable heat removal based upon the rate of condensation in the upstream working gas condensation apparatus 262. Variable heat removal is necessary to guarantee that a constant volume of condensed working gas is supplied to the throttling device 268. For example, a cell culture reactor may require different magnitudes of heat input to maintain temperature based upon its current life-cycle phase, thus creating a variable flow rate and phase of condensed working gas at the outlet of the working gas condensation apparatus 262. However, the implementation shown in FIG. 24 functions optimally with a constant heat load such that both the flow rate and phase of the working gas are identical at the input to each of the throttling device 268, the evaporator 266, and the compressor 264. Variable heat removal in the receiver 270 adds additional condensation to the system, when required, providing the downstream stability in phase and flow required.

Also, the alternative system 260 illustrated in FIG. 24 may be modified for use with a refrigerant vaporization apparatus. In this instance, the working gas condensation apparatus 262 and receiver with variable heat removal 270 are replaced by a traditional condenser, and the evaporator 266 is replaced by the refrigerant vaporization apparatus and receiver with variable heat addition. The receiver with variable heat addition serves a similar purpose as the receiver with variable heat removal 270, in that it helps to guarantee both a constant flow rate and phase of evaporated refrigerant to the downstream compressor 264, subject to the variable heat output of the medium to be cooled.

Figure 25:
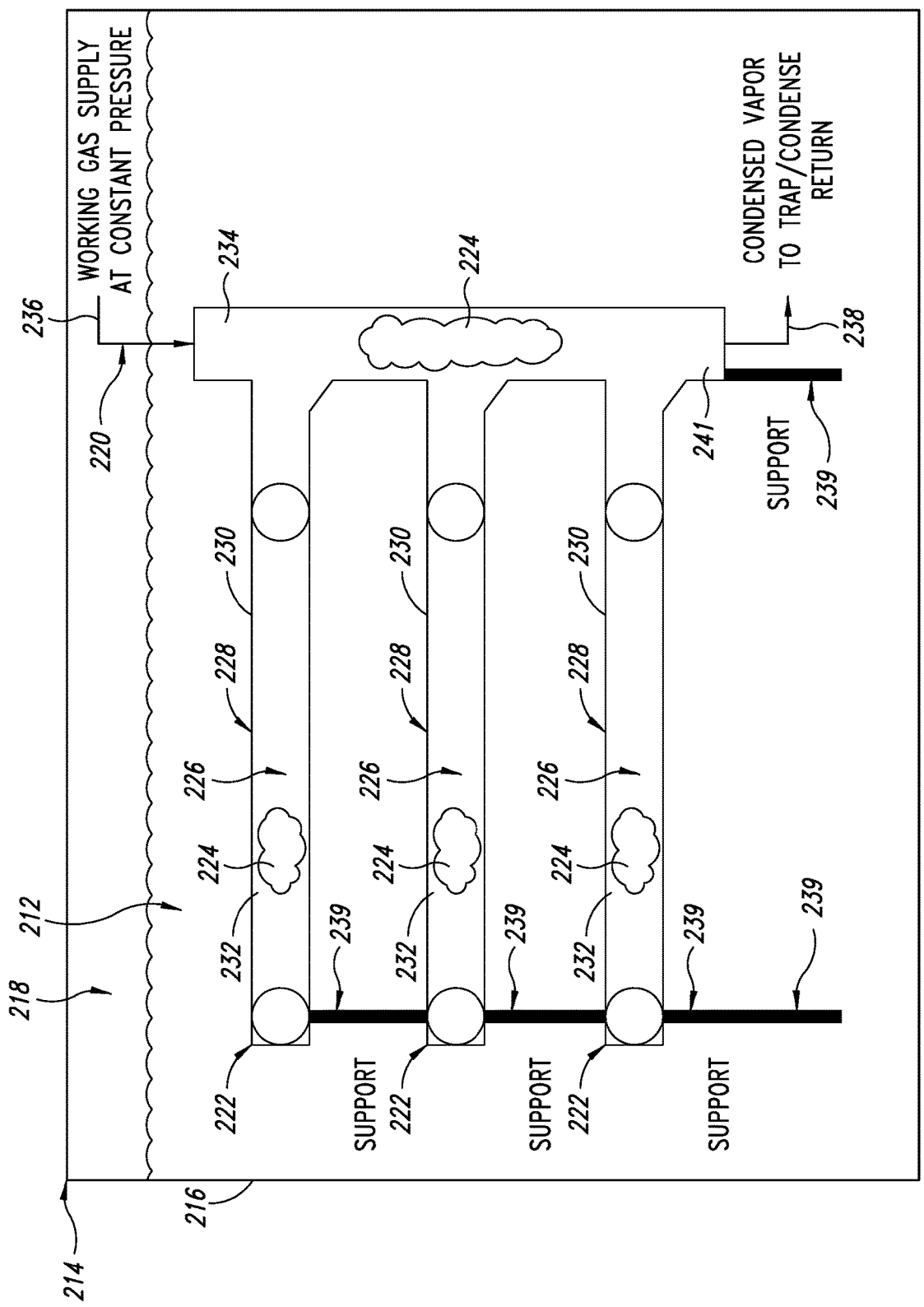
FIG. 25 is a side-elevational illustration in cross section of a working gas reservoir formed in accordance with the present disclosure and positioned in the interior of a container.
Figure 26:
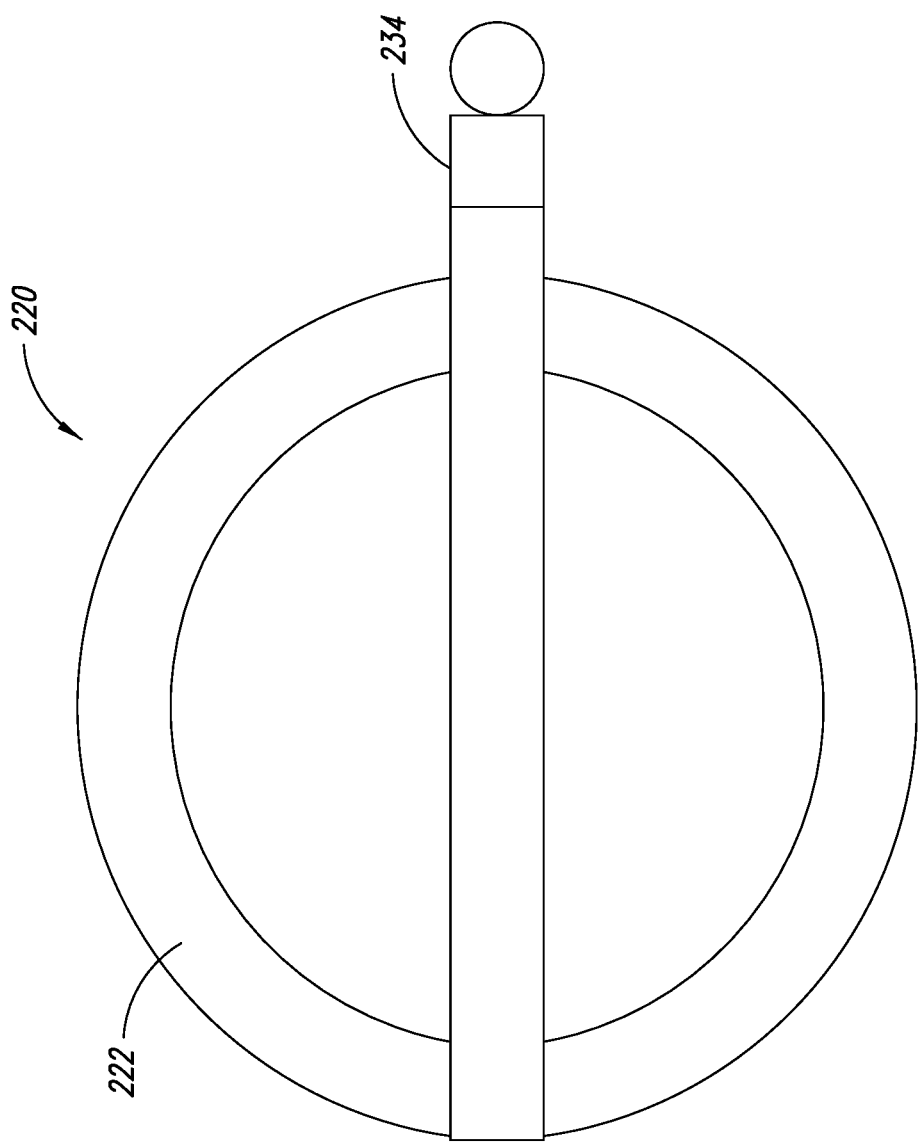
FIG. 26 is a top plan view of the working gas reservoir of FIG. 25.

As shown in FIG. 25, the working gas reservoir 220, in one implementation, has a manifold 234 coupled to each of the reservoir sections 222 to provide fluid communication to a working gas supply line 236 and to a condensate drain line 238, which allows for system liquid drain to the condensate trap 250 and condensate receiver 254. The plurality of reservoir sections 222 may be coupled together in series or in parallel or in a combination of series and parallel arrangements. The working gas reservoir 220, in one implementation, comprises a lattice of reservoir sections 222. Each reservoir section 222 is held in place by a vertical support 239, as is the manifold 234. Each reservoir section 222 is designed and positioned for gravity drain of condensed working gas to the condensate drain line 238 via sloping of a reservoir bottom 241.

Figure 27:
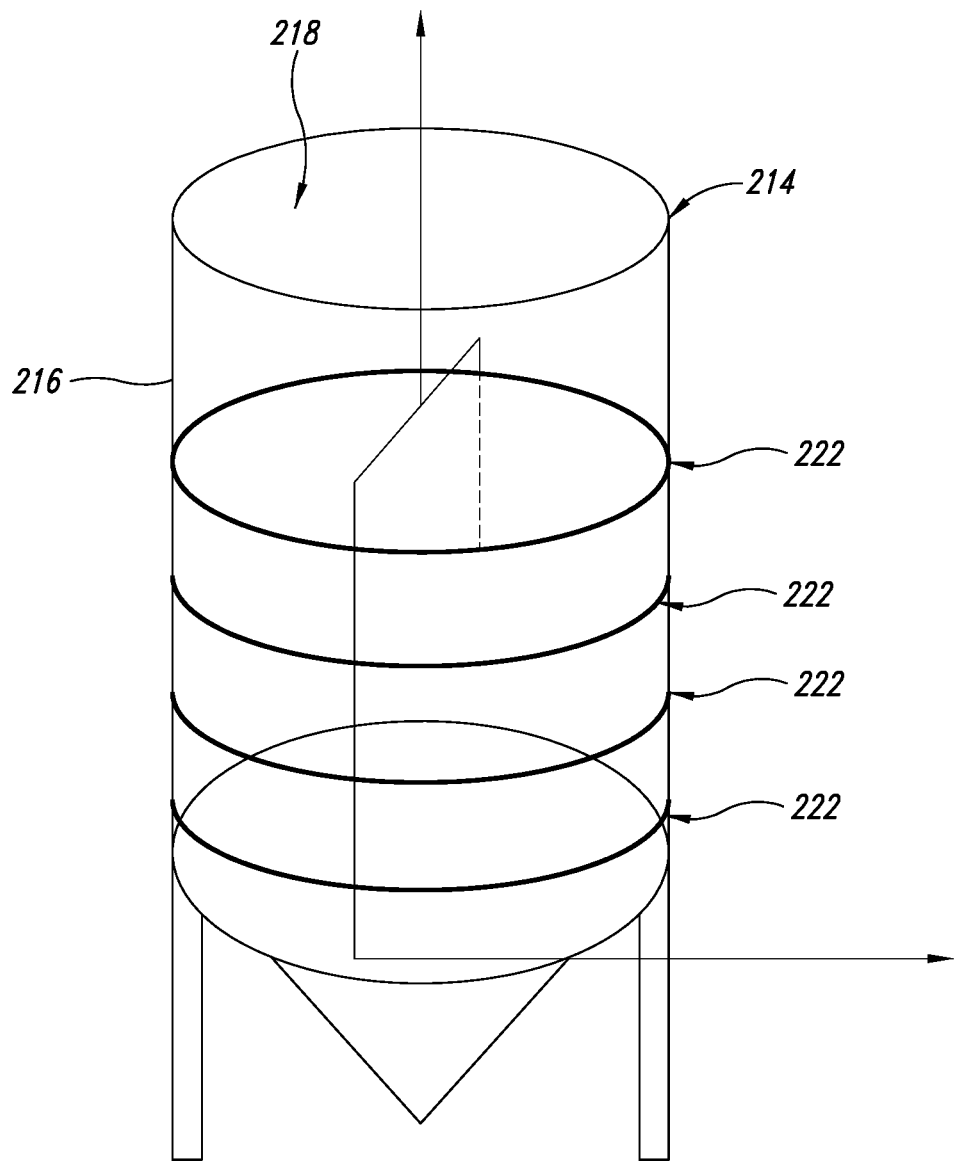
FIG. 27 is an illustration of a working gas reservoir on the exterior of a container in accordance with another implementation of the present disclosure.

In accordance with another aspect of the present disclosure, the working gas reservoir 220 may be located on the exterior of the container 214, which is shown in FIG. 27.

Figure 28:
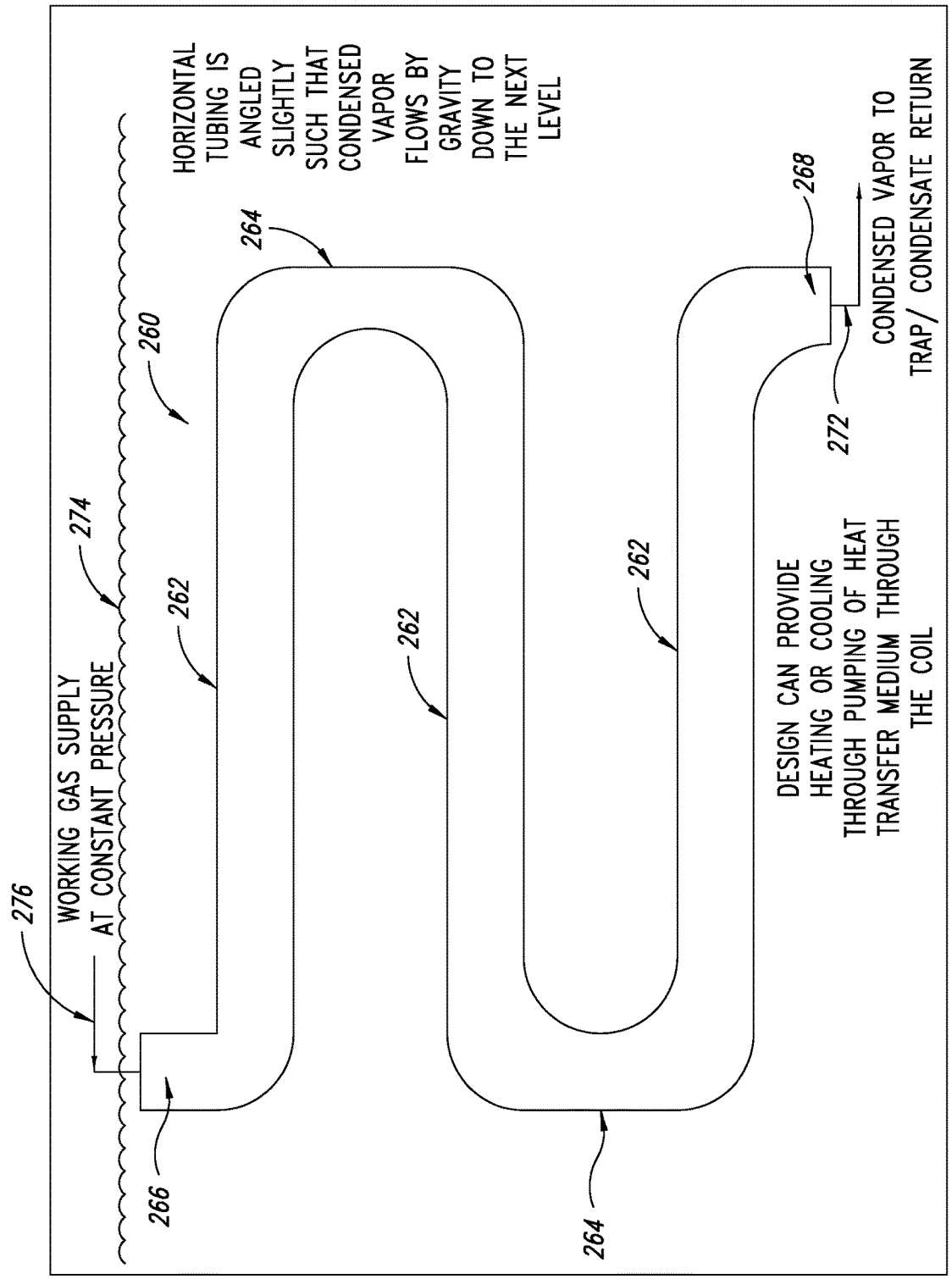
FIG. 28 is a side elevation cross-sectional illustration of a refrigerant reservoir formed in accordance with an alternative implementation of the apparatus in FIG. 25.

FIG. 28 shows an alternative implementation of the apparatus of FIG. 25. Here, a working gas reservoir 260 is provided that includes a plurality of reservoir sections 262 coupled in series by vertical risers 264 to form a continuous arrangement with an input port 266 at the top through which working gas 270 enters. A condensate drain line 268 is provided at the other end, which allows for system drain to the condensate trap 250 and condensate receiver 254. In this implementation, the working gas 270 enters the input port 266 at the top of the system and liquid condensate 272 is removed from the drain port 268 by gravity at the bottom. The working gas reservoir 260 must be sloped in the downward direction to promote gravity draining of condensate to the drain port 268. This coil would be suitable to use for heating or cooling of a medium via circulation of a heat transfer medium in either direction between the input port 266 and the drain port 268.

In operation, working gas 276 is introduced into the working gas reservoir 260 and the pressure of the working gas 276 in the working gas reservoir 260 is regulated to enable working gas condensation at or near a selected temperature of the volume of medium thermal coverage for the volume of the medium 274 in the container that is thermally coupled to the respective reservoir section 262.

System operation requires that the working gas condense at a uniform or, preferably, an identical temperature throughout the coil. Also, a working gas volume must be maintained throughout the coil, sufficient to remove the heat generated by the medium via vaporization. Proper orientation of the coil with respect to gravity ensures that the liquid volume of condensed working gas therein matches the design intent and drains quickly to the trap below, leaving the surface area of the coil interior without liquid obstructions that might reduce the condensation rate. The coil metallurgy must be selected so as not to adversely affect the quality of the medium to be warmed, and the coil should be cleaned between uses to avoid possible contamination of the new medium to be warmed. Working gas pressure should provide for working gas condensation at, or as close as possible to, the desired temperature of the medium to be warmed, so as to avoid possible thermal shock of the medium.

When utilizing gas cylinders for batch supply of the working gas, the working gas supply must be made available at a higher pressure than the coil demand, and system design must allow for variable inlet flow rates of the working gas to the system. This can be affected by use of an upstream accumulator which makes a large volume of working gas continually available, held at the desired pressure. The condensate trap and receiver must also be properly sized such that condensed working gas does not build to a high liquid level in the coil drain piping, obstructing the coil interior surface area available for heat transfer via condensation. The coil must be carefully oriented with respect to gravity, as well, to allow for proper draining and prevent liquid build-up in the horizontal sections.

When utilizing a compressor for continuous operation, proper orientation of the coil with respect to gravity ensures optimal system performance, as the working gas reservoirs drain condensed liquid by design. Compressor performance must be monitored relative to the heat production profile of the medium with respect to time. Most importantly, the compressor must be capable of continued operation at variable flowrates of condensed working gas and throughout the desired range of working gas inlet pressures. Cell cultures, for example, can vary in heat production rate as a function of both time and batch number. System monitoring must be sufficiently robust to adjust system operation to unexpected swings in process variables without risk of damage to the compressor and associated components.

Working gas selection is a function of the heat production profile and optimal production temperature of the medium to be heated relative to the choice of heating equipment and control scheme. Ideally, a working gas also condenses at a pressure greater than atmospheric (14.7 psia). This avoids the need to maintain a system environment below atmospheric pressure, particularly difficult as air leakage into the system is common through components and fittings and use of a vacuum source to compensate removes working gas from the coil before it has an opportunity to condense.

Pressure drop between the working gas source and coil must be calculated as a function of system geometry to ensure that the working gas will condense at the desired temperature. Operationally, the working gas pressure corresponds to the working gas condensation temperature, as this temperature is constant during the phase change. The objective is to control the pressure of the working gas in the coil at a specific condensation temperature, at or near that of the set-point temperature of the medium to be heated.

For fermentation of wine, common maximum allowable temperature ranges are 64-77° F. for red wines and 50-59° F. for whites. Assuming an R-134a working gas and compressor combination, these temperature ranges correspond to vapor pressures of approximately 77.10-96.11 psia for red wines and 59.98-70.61 psia for white wines. For fermentation of beer, common maximum allowable temperature ranges are 60-70° F. for ales and 45-55° F. for lagers. Assuming an R-134a working gas and compressor combination, these temperature ranges correspond to vapor pressures of approximately 71.87-85.48 psia for ales and 54.62-65.72 psia for lagers.

The system must also provide cooling for the duration of the fermentation cycle. For primary fermentation of both red and white wines, 3-5 days is commonly required. For primary fermentation of beer, 1-2 weeks is commonly required for ales and 1-2 months is commonly required for lagers.

8. Intermediate Medium on Coil Surface

The spacing equation for either the working gas reservoirs or refrigerant reservoirs can be modified to account for an intermediate medium to be placed in contact with both the surface of working gas reservoir or refrigerant reservoir and the medium. The intermediate medium may be useful as a disposable layer mounted on the exterior of the coil, for example, to prevent cross contamination from previous fermentations or as a method for changing the exterior metallurgy of the coil when a conflict exists between the coil metallurgy and the medium to be heated or cooled.

Sequentially, for a cooling coil, heat is conducted first from the medium to the intermediate medium, then from the intermediate medium to the wall of the coil, and finally through the coil wall to the refrigerant. For a heating coil, this heat transfer process is reversed with heat flow beginning at the working gas and ending at the medium. Quantitatively, the coil spacing equation is modified to account for the added resistance of the intermediate medium:

$$V = I * R \text{ Electrical Analogy}$$

$$\Delta T = Q * R \text{ Heat Transfer Equation}$$

$$\frac{\Delta T}{L} = \frac{Q * R}{L} \text{ Divide by Length of Horizontal Section}$$

$$\frac{Q}{L} = \frac{\Delta T}{R * L} \text{ Rearrange}$$

L=Length of horizontal lattice section (m);

Q=Total heat transferred from medium to horizontal section per unit time (W);

R=Total resistance to heat transfer across the temperature differential per unit time (K/W); and ΔT=Maximum temperature difference between medium and condensing working gas or vaporizing refrigerant (K).

$$\Delta T = T2 - T1 \text{ Temperature Differential } (K)$$

$$R = \left( \frac{1}{H1 * A1} + \frac{\ln\left(\frac{R2}{R1}\right)}{2 * \pi * L * K1} + \frac{\ln\left(\frac{R6}{R2}\right)}{2 * \pi * L * K4} + \frac{1}{H2 * A6} \right) \begin{array}{l} \text{Resistance to} \\ \text{Heat Transfer} \\ (K/W) \end{array}$$

$$R = \frac{1}{2 * \pi * L} * \left( \frac{1}{H1 * R1} + \frac{\ln\left(\frac{R2}{R1}\right)}{K1} + \frac{\ln\left(\frac{R6}{R2}\right)}{K4} + + \frac{1}{H2 * R6} \right) \text{Substituting}$$

$$R * L = \frac{1}{2 * \pi} * \left( \frac{1}{H1 * R1} + \frac{\ln\left(\frac{R2}{R1}\right)}{K1} + \frac{\ln\left(\frac{R6}{R2}\right)}{K4} + \frac{1}{H2 * R6} \right) \begin{array}{l} \text{Resistance} \\ \text{to Heat} \\ \text{Transfer} \\ \text{Across} \\ \text{Length} \\ (K * m/W) \end{array}$$

$$Q = J * (\pi * R3^2 * L - \pi * R6^2 * L) \begin{array}{l} \text{Heat Generated by Medium} \\ \text{per Unit Time for a} \\ \text{Horizontal Section } (W) \end{array}$$

-continued $$\frac{Q}{L} = J * \pi * (R3^2 - R6^2) \quad \begin{array}{l} \text{Heat Generated by Medium} \\ \text{per Length of Horizontal} \\ \text{Section per Unit Time } (W/m) \end{array}$$

A6=Surface area of exterior wall of the buffer medium enclosing surface (m²);
H1=Working gas or refrigerant heat transfer coefficient, including boundary layer effects (W/m²*K);
H2=Medium heat transfer coefficient, including boundary layer effects (W/m²*K);
J=Maximum heat generated or lost by medium per unit volume per unit time (W/m³);
K1=Thermal conductivity of lattice material of construction (W/m*K);
K4=Thermal conductivity of intermediate medium (W/m*K);
R1=Radius from center of horizontal lattice section to inside of lattice wall (m);
R2=Radius from center of horizontal lattice section to outside of lattice wall (m);
R3=Radius from center of horizontal lattice section to outside of medium volume (m);
R6=Radius from center of horizontal lattice section to outside of intermediate medium (m);
T1=Temperature at working gas or liquid-vapor refrigerant interface (K); and
T2=Temperature of medium at outer edge of medium volume (K).

$$\frac{Q}{L} * (R*L) - \Delta T = 0 \quad \begin{array}{l} \text{The Rearranged Heat Transfer} \\ \text{Equation Set Equal to Zero} \end{array}$$

$$J * \pi * (R3^2 - R6^2) * \frac{1}{2*\pi} *$$

$$\left( \frac{1}{H1*R1} + \frac{\ln\left(\frac{R2}{R1}\right)}{K1} + \frac{\ln\left(\frac{R6}{R2}\right)}{K4} + \frac{1}{H2*R6} \right) - (T2 - T1) = 0 \quad \text{Substituting}$$

$$R3 = \sqrt{\dfrac{\dfrac{1}{J*\pi}*(T2-T1)*}{\dfrac{1}{2*\pi}*\left(\dfrac{1}{H1*R1} + \dfrac{\ln\left(\dfrac{R2}{R1}\right)}{K1} + \dfrac{\ln\left(\dfrac{R6}{R2}\right)}{K4} + \dfrac{1}{H2*R6}\right)} + R6^2} \quad \text{Setting Equal to } R3$$

Figure 29:
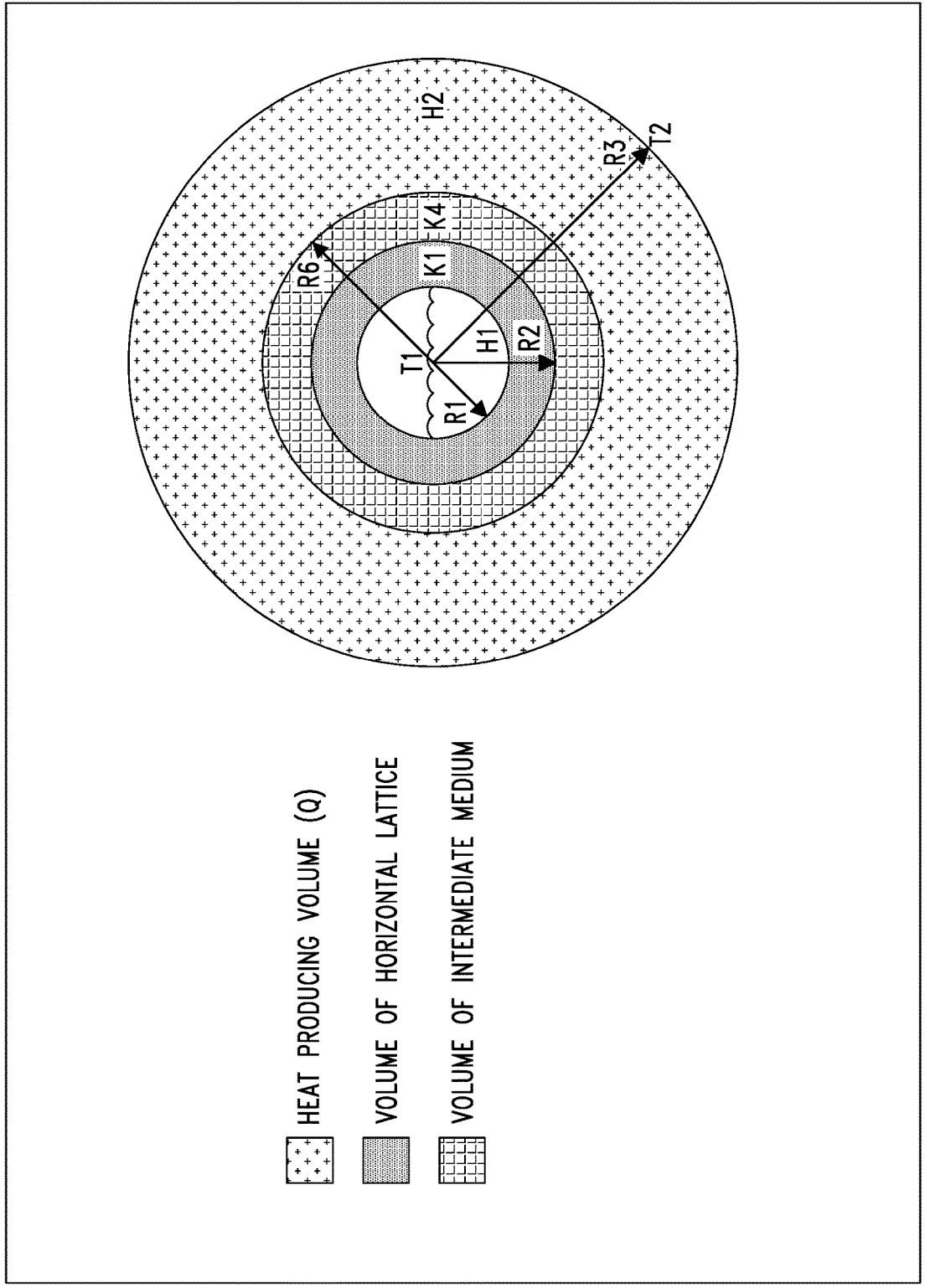
FIG. 29 is a cross-sectional illustration of radial heat transfer along a radius of a horizontal lattice section.

Referring to FIG. 29, for a given horizontal lattice section, the mechanical design must be capable of the desired heat transfer rate, subject to the added thermal resistances. Ideally, an intermediate medium will transport heat with minimal resistance and is of a material of construction favorable to the desired heat transfer rate. Also, the material of construction of the intermediate medium must be compatible with surrounding medium to be heated or cooled. Working gas reservoirs or refrigerant reservoirs including intermediate buffers may be located either interior or exterior to a tank or vessel.

9. Combination of Working Gas Condensation and Refrigerant Vaporization Coils

The refrigerant vaporization apparatus controls the temperature of a medium by preventing the medium volume from exceeding a high-bound temperature value. Utilizing the same coil spacing equation, the working gas condensation apparatus controls the temperature of a medium by preventing the medium volume from exceeding a low-bound temperature value. Both types of apparatuses can be combined inside a tank or vessel to control the temperature of the medium between a high-bound and low-bound value.

FIG. 30 is an illustration of adjacent refrigerant reservoirs designed such that the medium external to the reservoirs never exceeds a high-bound temperature of 72° F. FIG. 31 is an illustration of adjacent working gas reservoirs designed such that the medium external to the reservoirs never falls below a low-bound temperature of 68° F. The interior lattice temperature of the refrigerant and working gas reservoirs is 70° F.

FIG. 32 is an illustration of a combination of the refrigerant reservoirs shown in FIG. 30 and the working gas reservoirs shown in FIG. 31. The reservoirs are positioned such that the terminus of the volume of thermal coverage of one reservoir is located at the center of an adjacent reservoir of a different type. Thus, a refrigerant reservoir that prevents the temperature of the surrounding medium from exceeding between 70° F. and 72° F. is positioned such that its terminus of thermal coverage is located at the center of an adjacent working gas reservoir that prevents the temperature of the surrounding medium from falling below between 68° F. and 70° F.

Assuming radial heat transfer from each reservoir through an identical medium, there is minimal risk of interference between the two temperature control systems as the low bound temperature of the refrigeration vaporization apparatus never falls below the high bound temperature of the working gas condensation apparatus and the high bound temperature of the working gas condensation apparatus never exceeds the low bound temperature of the refrigeration vaporization apparatus. Accordingly, no spatial temperature gradient is formed by which the condensation apparatus would provide heat to the vaporization apparatus volume of cooling coverage, and no spatial temperature gradient is formed by which the vaporization apparatus would remove heat from the condensation apparatus volume of cooling coverage.

10. Use of Working Gas Condensation and Refrigerant Vaporization Coils Inside Agitated Tanks The refrigerant vaporization apparatus controls the temperature of a medium by preventing the medium volume from exceeding a high-bound temperature value. Utilizing the same coil spacing equation, the working gas condensation apparatus controls the temperature of a medium by preventing the medium volume from exceeding a low-bound temperature value. Both types of apparatuses can be used individually to control the temperature of a medium inside a tank or vessel or combined inside a tank or vessel to control the temperature of the medium at or between a high-bound and low-bound value.

Use of either or both apparatuses in agitated tanks improves the probability that heat is successfully transferred either from the medium to the refrigerant vaporization reservoir or from the working gas condensation reservoir to the medium. Mathematically, this probability increase is manifested by an increase in H2, the medium heat transfer coefficient including boundary layer effects. Per the coil spacing equation, an increase in H2 then increases the value of R3, the radius from center of horizontal lattice section to outside of medium volume. Practically, use of agitation in a tank or vessel reduces the coil surface area required to maintain the desired volumes of cooling coverage inside a tank or vessel. For example, a refrigerant vaporization apparatus used in wine fermentation with ethanol refrigerant, 2" OD sanitary reservoir tubing reservoirs, and a 10° F. temperature differential has an ideal lattice spacing of roughly 12 inches. If the wine tank or vessel was agitated, the value of H2, the medium heat transfer coefficient including boundary layer effects, could increase from 140 W/m^2*K to 1000 W/m^2*K. Per the spacing equation, this change changes the ideal lattice spacing to roughly 21 inches.

It is often useful to further subdivide H1, the refrigerant or condensing working gas heat transfer coefficient including boundary layer effects, and H2, the medium heat transfer coefficient including boundary layer effects. This subdivision allows for improved analysis of the effects of agitation on heat transfer rate. For example, if lattice spacing is increased due to medium agitation, fouling then has a greater proportional effect on heat transfer as there is less coil surface area available. Impeller design, speed, and spatial location may also have significant impact on coil heat transfer rate in agitated tanks or vessels through changes in the heat transfer film coefficient. A representative subdivision for an agitated refrigerant vaporization apparatus is as follows:

$$1/U = 1/HM + 1/HROFC + 1/HROF + 1/HR + 1/HRIF + 1/HRIFC + 1/HF$$

$U$=Overall heat transfer coefficient (W/m^2*K);
$HM$=Medium heat transfer coefficient (W/m^2*K);
$HROFC$=Reservoir outer film heat transfer coefficient (W/m^2*K);
$HROF$=Reservoir outer fouling heat transfer coefficient (W/m^2*K);
$HR$=Reservoir heat transfer coefficient (W/m^2*K);
$HRIF$=Reservoir inner fouling heat transfer coefficient (W/m^2*K);
$HRIFC$=Reservoir inner film heat transfer coefficient (W/m^2*K); and
$HF$=Refrigerant heat transfer coefficient (W/m^2*K).

Note that U, the overall heat transfer coefficient, now represents the complete heat transfer rate from the medium to the refrigerant, accounting for the effects of H1, H2, and K1, thermal conductivity of lattice material of construction, as used in the spacing equation.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A method of controlling temperature in a medium stored in a container, the method comprising:
partitioning the medium into localized thermal volumes and positioning at least one working gas reservoir in physical proximity to the container, the at least one working gas reservoir having at least one reservoir section configured to hold gas, wherein the at least one reservoir section comprises a plurality of reservoir sections that each have a respective internal reservoir space that is in fluid communication with at least one other internal reservoir space of adjacent reservoir section, and the plurality of reservoir sections arranged in spaced relationship to adjacent reservoir sections with the respective volumes of medium thermal coverage having the respective boundaries of thermal coverage to be at least contiguous; and
thermally coupling a working gas to respective localized thermal volumes to control a temperature of the localized thermal volume to maintain the medium at a selected temperature.

2. The method of claim 1 further comprising coupling together the plurality of reservoir sections in parallel or in a combination of series and parallel arrangements.

3. The method of claim 1 further comprising configuring the plurality of reservoir sections in a lattice of reservoir sections.

4. The method of claim 1 further comprising locating at least one working gas reservoir in the interior of the container.

5. The method of claim 1 wherein the thermally coupling comprises regulating working gas pressure in each at least one reservoir section to maintain a temperature of the respective localized thermal volume at the selected temperature of the medium.

6. The method of claim 5 wherein the regulating working gas pressure comprises providing a condensation apparatus to provide regulation of working gas pressure in the at least one working gas reservoir.

7. The method of claim 6 further comprising configuring the at least one working gas reservoir to form a vapor space in each of the at least one reservoir sections in response to receiving working gas and in response to the condensation apparatus regulation of working gas pressure to enable working gas condensation at or near a selected temperature of the volume of medium thermal coverage for the volume of the medium in the container that is thermally coupled to the respective at least one reservoir section.

8. A method of controlling a temperature of a medium by working gas condensation, the method comprising:
providing an apparatus for controlling the temperature of the medium by condensation of a working gas, the providing including providing:
a container having an exterior and an interior;
at least one working gas associated with the container, at least one working gas reservoir having at least one reservoir section configured to hold working gas, each at least one reservoir section having a wall with an exterior surface structured to be thermally coupled with a volume of the medium in the container and to provide thermal change to the volume of the medium in the container and thereby provide a volume of medium thermal coverage in the container, the volume of medium thermal coverage having an outside boundary;
a condensation apparatus to provide regulation of working gas pressure in the at least one working gas reservoir;
wherein the at least one working gas reservoir is configured to form a vapor space in each of the at least one reservoir sections in response to receiving working gas and in response to the condensation apparatus regulation of working gas pressure to enable working gas condensation at or near a selected temperature of the volume of medium thermal coverage for the volume of the medium in the container that is thermally coupled to the respective at least one reservoir section;
introducing working gas into the at least one working gas reservoir to partially occupy the at least one reservoir section in the at least one reservoir section; and regulating working gas pressure in the at least one reservoir section to enable working gas condensation at or near a selected temperature of the volume of medium thermal coverage for the volume of the medium in the container that is thermally coupled to the respective at least one reservoir section;

wherein the at least one reservoir section comprises a plurality of reservoir sections that each have a respective internal reservoir space that is in fluid communication with at least one other internal reservoir space of an adjacent reservoir section, and the plurality of reservoir sections arranged in spaced relationship to adjacent reservoir sections with the respective volumes of medium thermal coverage having the respective boundaries of thermal coverage to be at least contiguous.

9. A method of controlling a temperature of a medium by refrigerant vaporization, the method comprising:

providing an apparatus for controlling the temperature of the medium by refrigerant vaporization of a refrigerant, the providing including providing:

a container having an exterior and an interior;

at least one a refrigerant reservoir associated with the container, the at least one refrigerant reservoir having at least one reservoir section configured to hold refrigerant, each at least one reservoir section having a wall with an exterior surface structured to be thermally coupled with a volume of the medium in the container and to provide thermal change to the volume of the medium in the container and thereby provide a volume of medium thermal coverage in the container, the volume of medium thermal coverage having an outside boundary;

a vapor pressure apparatus to provide regulation of refrigerant vapor pressure in the at least one refrigerant reservoir;

wherein the at least one refrigerant reservoir is configured to form a vapor space in each of the at least one reservoir sections in response to receiving refrigerant and in response to the vapor pressure apparatus regulation of vapor pressure above the refrigerant to enable refrigerant vaporization at or near a selected temperature of the volume of medium thermal coverage for the volume of the medium in the container that is thermally coupled to the respective at least one reservoir section;

introducing refrigerant into the at least one refrigerant reservoir to partially occupy the at least one refrigerant section and form a vapor space in the at least one refrigerant section; and regulating vapor pressure above the refrigerant in the at least one refrigerant reservoir to enable refrigerant vaporization at or near a selected temperature of the volume of medium thermal coverage for the volume of the medium in the container that is thermally coupled to the respective at least one reservoir section;

wherein the at least one reservoir section comprises a plurality of reservoir sections that each have a respective internal reservoir space that is in fluid communication with at least one other internal reservoir space of an adjacent reservoir section, and the plurality of reservoir sections arranged in spaced relationship to adjacent reservoir sections with the respective volumes of medium thermal coverage having the respective boundaries of thermal coverage to be at least contiguous.

10. A system to control a temperature of a medium comprising:

a container having an exterior and an interior;

at least one reservoir associated with the container, the at least one reservoir having at least one reservoir section configured to hold a substance, each at least one reservoir section having a wall with an exterior surface structured to be thermally coupled with a volume of the medium in the container and to provide thermal change to the volume of the medium in the container and thereby provide a volume of medium thermal coverage in the container, the volume of medium thermal coverage having an outside boundary;

an apparatus to provide regulation of substance pressure in the at least one reservoir;

wherein the at least one reservoir is configured to form a vapor space in each of the at least one reservoir sections in response to receiving substance and in response to the apparatus regulation of the substance pressure to enable a phase change of the substance at or near a selected temperature of the volume of medium thermal coverage for the volume of the medium in the container that is thermally coupled to the respective at least one reservoir section; and wherein the at least one reservoir section comprises a plurality of reservoir sections that each have a respective internal reservoir space that is in fluid communication with at least one other internal reservoir space of an adjacent reservoir section, and the plurality of reservoir sections arranged in spaced relationship to adjacent reservoir sections with the respective volumes of medium thermal coverage having the respective boundaries of thermal coverage to be at least contiguous.

11. The system of claim 10, further comprising a substance source in fluid communication with the reservoir and the apparatus, and configured to provide the substance to the reservoir in response to a change in pressure in the reservoir as regulated by the apparatus.

12. The system of claim 10, wherein the plurality of reservoir sections are coupled together in series or in parallel or in a combination of series and parallel arrangements.

13. The system of claim 10 wherein the reservoir comprises a lattice of reservoir sections.

14. The system of claim 10, in which R3 is a radius of the volume of medium thermal coverage that is determined as follows:

$$R3 = \sqrt{\frac{\frac{1}{J*\pi}*(T2-T1)*\frac{1}{1}}{\frac{1}{2*\pi}*\left(\frac{1}{H1*R1}+\frac{\ln\left(\frac{R2}{R1}\right)}{K1}+\frac{1}{H2*R2}\right)}+R2^2}$$

where:

H1=Substance heat transfer coefficient, including boundary layer effects (W/m$^2$*K);

H2=Medium heat transfer coefficient, including boundary layer effects (W/m$^2$*K);

J=Heat generated by medium per unit volume per unit time (W/m$^3$);

K1=Thermal conductivity of reservoir wall material of construction (W/m*K);

R1=Radius from center of reservoir section to interior of reservoir section wall (m);
R2=Radius from center of reservoir section to exterior of reservoir section wall (m);
R3=Radius from center of reservoir section to outside boundary of medium thermal coverage (m);
T1=Temperature of substance at a location of phase change (K); and
T2=Temperature of the medium at an outer boundary of thermal coverage (K).

15. The system of claim 14 wherein a minimum spacing between a center of adjacent reservoir sections is not less than $$\frac{2}{\sqrt{2}} * R3$$

and in which R3 is a radius of the volume of medium thermal coverage.

16. The system of claim 10 wherein the at least one reservoir is located in the interior of the container.

17. The system of claim 10 wherein the at least one reservoir is located on the exterior of the container.

18. The system of claim 10 further comprising a variable speed pump for moving the substance through the reservoir and apparatus.

19. The system of claim 10 further comprising a compressor for moving the substance through the reservoir and apparatus.

\* \* \* \* \*

UNITED STATES PATENT AND TRADEMARK OFFICE
CERTIFICATE OF CORRECTION

Page 1 of 1

PATENT NO. : 12,163,703 B2
APPLICATION NO. : 18/335750
DATED : December 10, 2024
INVENTOR(S) : Thomas U. Abell It is certified that error appears in the above-identified patent and that said Letters Patent is hereby corrected as shown below:

In the Claims

Column 37, Claim 9, Line 23:
"at least one a refrigerant" should read: --at least one refrigerant--.

Signed and Sealed this
Eleventh Day of February, 2025

Coke Morgan Stewart
*Acting Director of the United States Patent and Trademark Office*